United States Patent [19]
Fisher et al.

[11] Patent Number: 5,569,230
[45] Date of Patent: Oct. 29, 1996

[54] INDIVIDUALLY PACKAGED SANITARY NAPKIN HAVING CLEANING WIPE PACKAGED THEREWITH

[75] Inventors: Daniella J. Fisher; Thomas W. Osborn, III; Mark D. Seymour; Gary W. Kingry; Charles J. Berg, Jr., all of Cincinnati; Charles D. Cook, Fairfield; Steven R. Gilbert; Douglas Toms, both of Cincinnati, all of Ohio

[73] Assignee: The Procter & Gamble Company, Cincinnati, Ohio

[21] Appl. No.: 453,326

[22] Filed: May 30, 1995

Related U.S. Application Data

[63] Continuation of Ser. No. 346,985, Nov. 30, 1994, abandoned, which is a continuation of Ser. No. 874,871, Apr. 28, 1992, abandoned, which is a continuation-in-part of Ser. No. 795,932, Nov. 15, 1991, Pat. No. 5,484,636, which is a continuation-in-part of Ser. No. 533,614, Jun. 5, 1990.

[51] Int. Cl.⁶ ............................ A61F 13/15; A61B 17/06
[52] U.S. Cl. ............... 604/385.1; 604/387; 604/389; 604/390; 206/438
[58] Field of Search ................... 206/438–440; 604/359–360, 385.1–387, 389–390

[56] References Cited

U.S. PATENT DOCUMENTS

| | | | |
|---|---|---|---|
| 2,834,459 | 5/1958 | Rickard et al. | 206/440 |
| 3,967,729 | 7/1976 | Tanner, II | 206/440 |
| 3,973,567 | 8/1976 | Srinivasan et al. | 604/385.1 |
| 4,192,299 | 3/1980 | Sabatano | 604/360 |
| 4,221,221 | 9/1980 | Ehrlich | 604/386 |
| 4,556,146 | 12/1985 | Swanson et al. | 604/385.1 |
| 4,702,378 | 10/1987 | Finkel et al. | 604/385.1 |
| 4,738,678 | 4/1988 | Paulis | 604/385.1 |
| 4,743,240 | 5/1988 | Powell | 604/385.1 |
| 4,781,712 | 11/1988 | Barabino et al. | 604/385.1 |
| 4,790,840 | 12/1988 | Cortina | 604/385.1 |
| 4,808,178 | 2/1989 | Hansen | 604/385.1 |
| 4,848,572 | 7/1989 | Herrera | 206/438 |
| 4,917,675 | 4/1990 | Taylor et al. | 604/385.1 |
| 4,931,052 | 6/1990 | Feldman | 206/438 |
| 5,088,993 | 2/1992 | Gaur | 604/385.1 |
| 5,484,636 | 1/1996 | Berg, Jr. et al. | |

FOREIGN PATENT DOCUMENTS

| | | | |
|---|---|---|---|
| 0350924 | 1/1990 | European Pat. Off. | 604/385.1 |

*Primary Examiner*—John G. Weiss
*Assistant Examiner*—K. M. Reichle
*Attorney, Agent, or Firm*—Jeffrey V. Bamber; Edward J. Milbrada; Steven W. Miller

[57] ABSTRACT

An individually packaged sanitary napkin having a cleansing wipe packaged therewith. The individually packaged sanitary napkin includes a wrapper that covers the sanitary napkin's adhesive fastener prior to use. The sanitary napkin wrapper can be provided with a flap or pouch for securing the used sanitary napkin for disposal. A number of alternative arrangements are disclosed for packaging the cleansing wipe with the wrapped sanitary napkin.

14 Claims, 10 Drawing Sheets

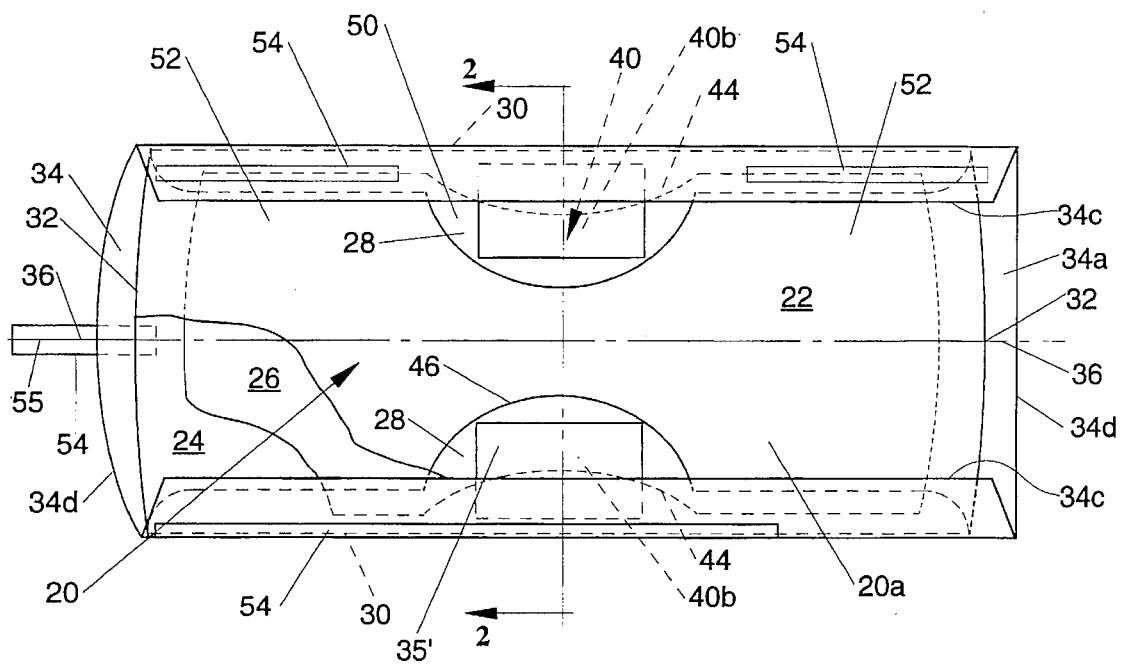
Fig. 1
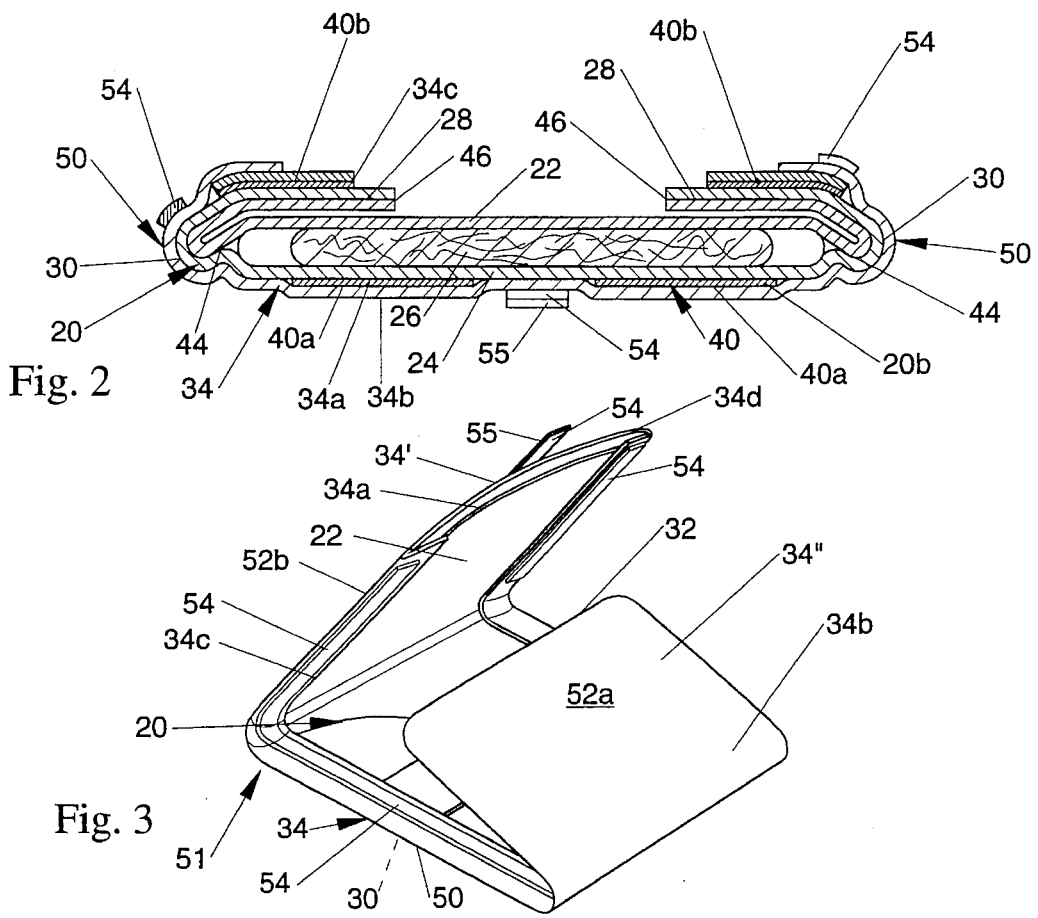
Fig. 2
Fig. 3

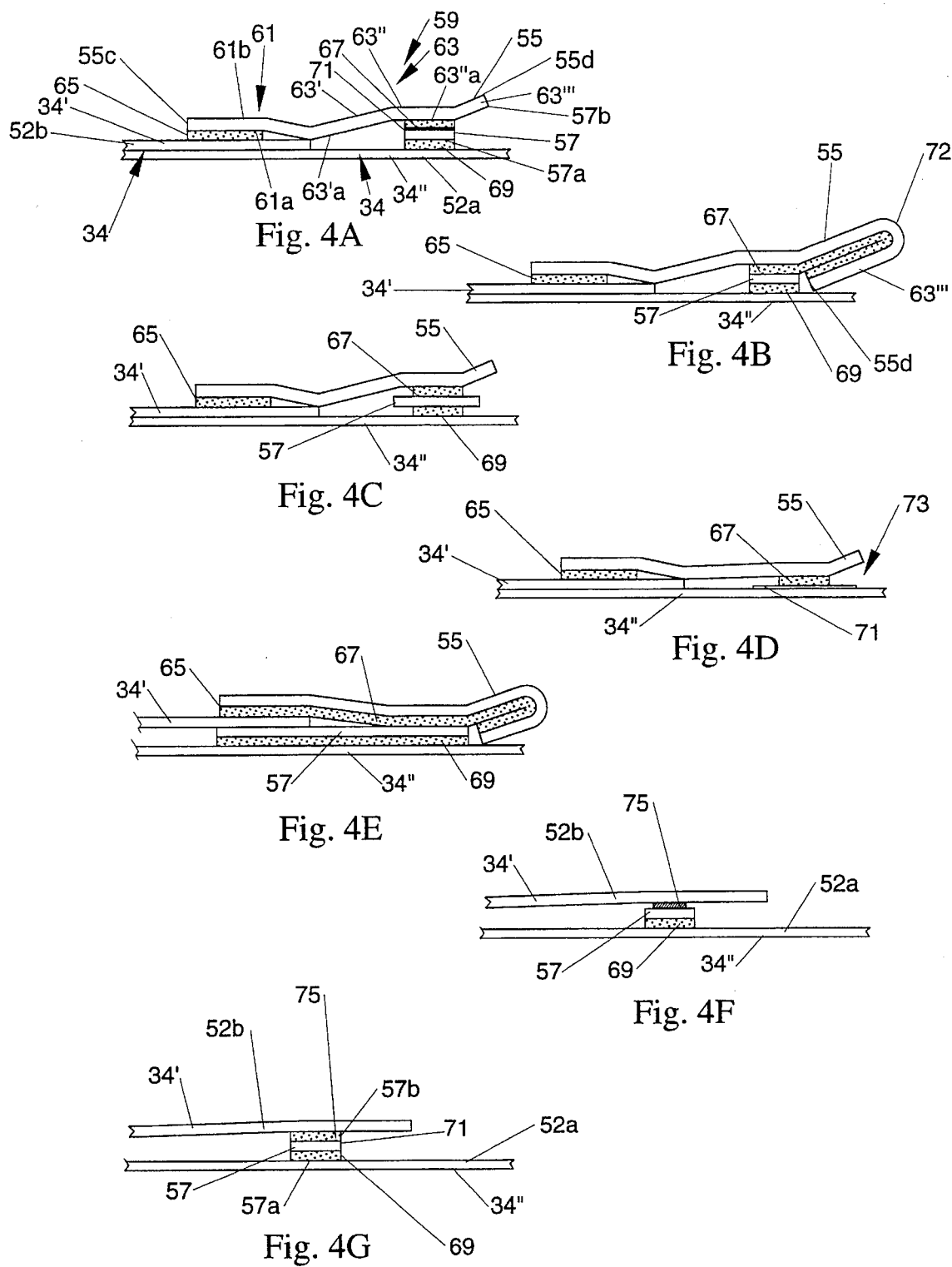

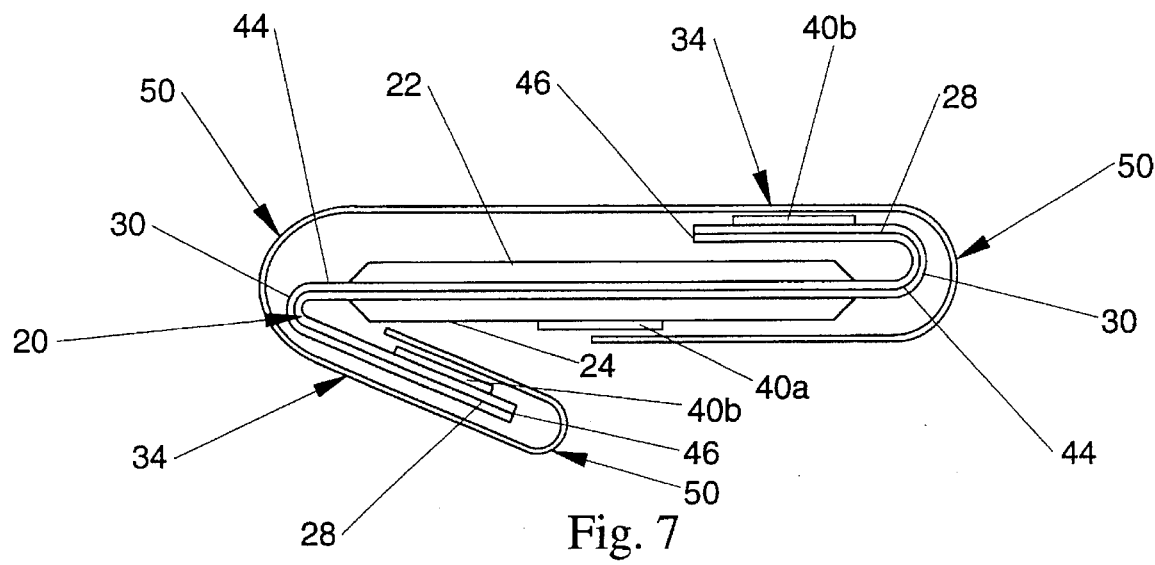
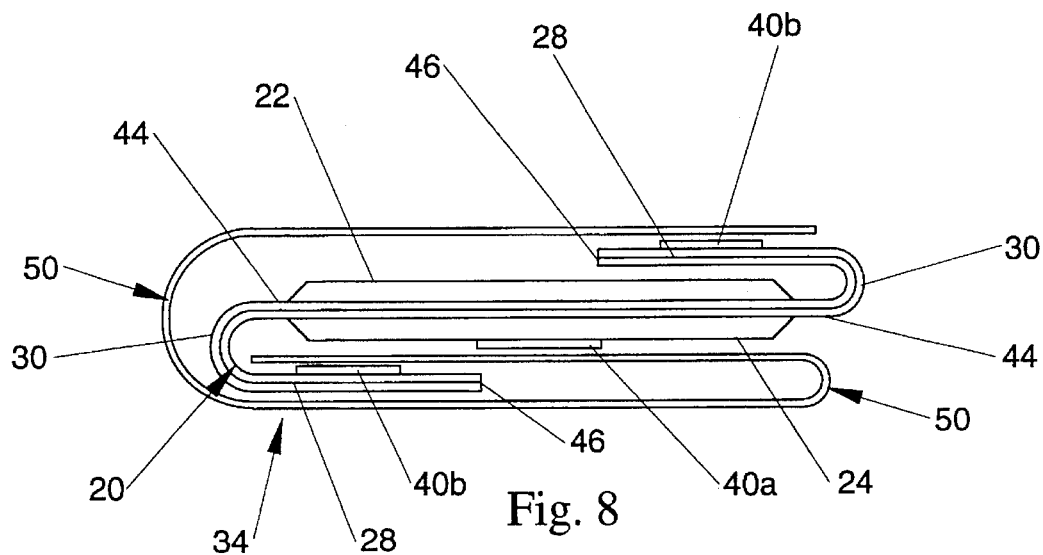
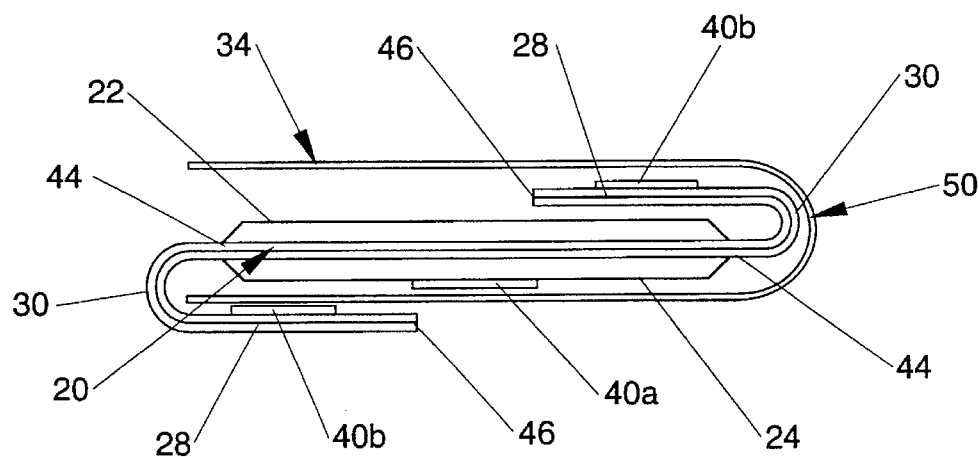

INDIVIDUALLY PACKAGED SANITARY NAPKIN HAVING CLEANING WIPE PACKAGED THEREWITH

This application is a continuation of application Ser. No. 08/346,985, filed on Nov. 30, 1994, now abandoned; which application is a continuation of application Ser. No. 07/874,871, filed on Apr. 28, 1992, now abandoned; which application is a continuation-in part of application Ser. No. 07/795,932, filed on Nov. 15, 1991, now U.S. Pat. No. 5,484,636; which application is a continuation-in-part of application Ser. No. 07/533,614, filed on Jun. 5, 1990, now pending as application Ser. No. 08/459,372, filed on Jun. 2, 1995.

FIELD OF THE INVENTION

This invention is directed to individually packaged sanitary napkins and more particularly to individually packaged sanitary napkins having a cleansing wipe packaged therewith.

BACKGROUND OF THE INVENTION

Sanitary napkins used to collect vaginal discharges are well known in the art. Individually packaged sanitary napkins are also known.

Individually packaged sanitary napkins are disclosed in U.S. Pat. No. 3,035,578 issued to Elmore on May 22, 1962; U.S. Pat. No. 3,604,423, issued Sep. 14, 1971 to Fraser, U.S. Pat. No. 3,973,567, issued to Srinivasan, et al. on Aug. 10, 1976; U.S. Pat. No. 4,556,146, issued Dec. 3, 1985, to Swanson et al. International Publication WO 89/02728 published Apr. 6, 1989 in the name of Froidh et al.; U.S. Pat. No. 4,917,675, issued to Taylor, et al. on Apr. 17, 1990; European Patent Application Publication No. 0357000 A1 published in the name of Umesh Gaur on Mar. 7, 1990; and in U.S. Pat. No. 5,088,993, issued to Gaur on Feb. 18, 1992.

Discarding used sanitary napkins enveloped in the packaging is taught in the art. For example, International Publication WO 89/02729 published Apr. 6, 1989 in the name of Pigneul and U.S. Pat. No. 4,608,047, issued Aug. 26, 1986 to Mattingly disclose two packaging arrangements that can be used for this purpose.

Packaging cleansing wipes with sanitary napkins, or absorbent articles of different types is also known in the art. U.S. Pat. No. 4,738,678, issued to Paulis on Apr. 19, 1988 discloses packaging a cleansing sheet with a disposable diaper. The above-mentioned U.S. Pat. No. 4,917,675 issued to Taylor, et al. discloses, but does not illustrate one sanitary napkin packaging arrangement. As a result of the lack of an illustration, however, it is not clear what type of packaging arrangement is described in the Taylor, et al. patent.

The search for improved individual package configurations for sanitary napkins has, therefore, continued.

Accordingly, it is an object of this invention to provide an individually packaged sanitary napkin. It is further an object of this invention to provide individually packaged sanitary napkin with packaging that protects the exposed adhesive on the napkin prior to the first use by the wearer. It is also an object of this invention to provide an individually packaged sanitary napkin having a cleansing wipe packaged therewith. It is also an object of this invention to provide an individually packaged sanitary napkin having packaging which may be used for disposal of a used product. Finally, it is an object of this invention to provide improved closure mechanisms for maintaining the package in a closed configuration for disposal.

BRIEF SUMMARY OF THE INVENTION

The present invention comprises an individually packaged sanitary napkin having two longitudinal and two end edges. The sanitary napkin has a liquid pervious topsheet, a liquid impervious backsheet having opposed inwardly and outwardly oriented faces joined to the topsheet, an adhesive patch on the outwardly oriented face of the backsheet and an absorbent core positioned between the topsheet and the backsheet.

The individually packaged sanitary napkin may, in at least one embodiment, comprise a releasable wrapper releasably affixed to the adhesive patch on the outwardly oriented face of said backsheet. In at least one such embodiment, the wrapper is folded about at least two transverse axes to define a package body and a package flap. The releasable wrapper is provided with a flap or pouch at one end. The flap has sides that are sealed. At least one of the sides is sealed with an openable seal. The individually packaged sanitary napkin has a liquid-containing cleansing wipe associated therewith. In the above embodiment, the cleansing wipe may be positioned inside the flap. The flap or pouch may also be used in the disposal of a used sanitary napkin. The sanitary napkin wrapper can be provided with a tape tab for securing the wrapper around the sanitary napkin prior to use and/or for disposal of a used sanitary napkin.

In other embodiments, the cleansing wipe is placed in a separate receptacle that is associated with the releasable wrapper that forms the sanitary napkin package. In a variation of this embodiment, the receptacle can be large enough to cover the adhesive patch and serve as a release paper for the adhesive patch. In other embodiments, the cleansing wipe may be laminated between the releasable wrapper and a film. In still other embodiments, the sanitary napkin may be provided with a release paper strip, folded, and placed in a package having a package body and a package flap. In this latter embodiment, the cleansing wipe can be placed in a pouch located on the package or in a separate receptacle associated with the package.

BRIEF DESCRIPTION OF THE DRAWINGS

While the specification concludes with claims particularly pointing out and distinctly claiming the present invention, it is believed the invention will be better understood from the following description taken in conjunction with the accompanying drawings.

FIG. 1 is a top plan view (with a portion of the napkin and wrapper cut away) of a flapped sanitary napkin and releasable wrapper, according to the present invention, and showing a different adhesive configuration at each longitudinal edge of the releasable wrapper.

FIG. 2 is a vertical sectional view taken along lines 2—2 of FIG. 1.

FIG. 3 is a perspective view of a wrapper and a sanitary napkin in a partially trifolded configuration.

FIG. 4A is a side view of a preferred adhesive tab construction.

FIGS. 4B–4G are side views of some alternatively preferred adhesive tabs.

FIG. 7 is an endwise vertical elevational view of a sanitary napkin having one flap folded over the topsheet, one flap folded over the backsheet, and a releasable wrapper which C-folds both faces of one flap and both longitudinal side margins.

FIG. 8 is an endwise vertical elevational view of a sanitary napkin having one flap folded over the topsheet, one flap folded over the backsheet, and a releasable wrapper which encases both faces of one flap and resembles an e-fold.

FIG. 9 is an endwise vertical elevational view of a sanitary napkin having one flap folded over the topsheet, one flap folded over the backsheet, with one flap being inside the releasable wrapper and one flap being outside the releasable wrapper.

DETAILED DESCRIPTION OF THE INVENTION

Figure 4:
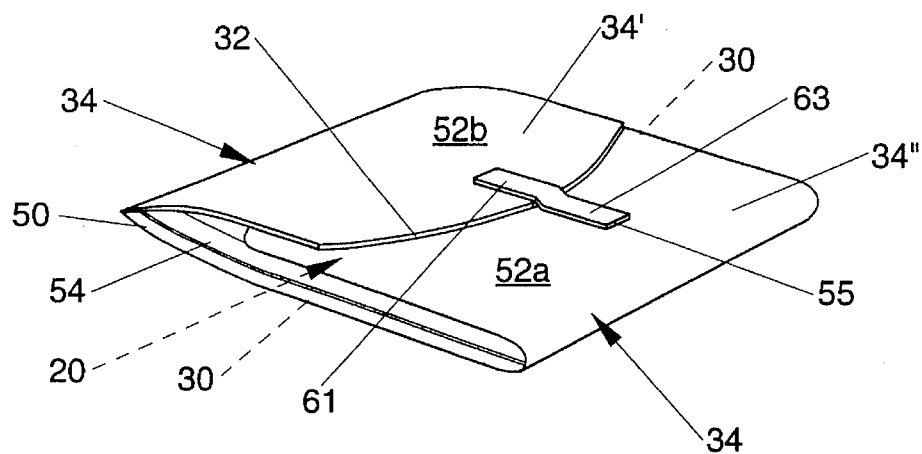
FIG. 4 is the sanitary napkin and wrapper according to FIG. 3 shown in a fully trifolded configuration.

The present invention is directed to an individually packaged, absorbent article, such as a sanitary napkin, and more particularly to an individually packaged sanitary napkin having a cleansing wipe packaged therewith.

FIG. 1 shows in conjunction with one form of package a sanitary napkin designated 20. The sanitary napkin 20 is used to collect vaginal discharges, such as menses, and to prevent soiling of the wearer's clothing by such discharges. The sanitary napkin 20 has a body-facing side or face 20a and an opposed garment-facing side or face 20b (shown in FIG. 2). The sanitary napkin 20 features a liquid pervious topsheet 22, a liquid impervious backsheet 24, and an absorbent core 26 intermediate the topsheet 22 and the backsheet 24. The perimeter of the central portion of the sanitary napkin 20 is defined by the two longitudinal side margins (or "side edges") 30 and two lateral side margins (or "end edges" or "ends") 32.

If desired, the sanitary napkin 20 may further comprise at least one flap 28 extending from a longitudinal side margin 30 of the sanitary napkin 20, and preferably two symmetrically opposite flaps 28, one extending from each longitudinal side margin 30 of the sanitary napkin 20.

The sanitary napkin 20 is superimposed on a releasable wrapper (or "release paper wrap") 34. (The releasable wrapper need not be paper, however.) The releasable wrapper 34 underlays and is releasably affixed to the outwardly oriented face of the backsheet 24. As used herein, "releasably affixed" refers to the condition of two or more components which may be attached and separated without destruction of or undue distortion to either component. In the embodiment shown, the releasable wrapper 34 is slightly larger than the central portion of the sanitary napkin 20 as it is defined by the longitudinal and lateral side margins 30 and 32.

Associated with the sanitary napkin 20 and each flap 28 is a means 40 for attaching the sanitary napkin 20 to the undergarment of a wearer. FIG. 2 shows that the central portion of the sanitary napkin 20 laterally intermediate the flaps 28 has adhesive 40a associated with the portion of the sanitary napkin 20 which contacts the undergarment of the wearer. Each flap 28 may also have its own adhesive patch 40b associated with the face of the flap 28 which contacts the undergarment of the wearer. Preferably such adhesives 40a and 40b are joined to the outwardly oriented face of the backsheet 24.

The releasable wrapper 34 contacts the adhesive 40a of the central portion of the backsheet 24, and if desired, the adhesive 40b of the flaps 28, to prevent contamination of such adhesive 40 prior to first use by the wearer. Also, the releasable wrapper 34 prevents the exposed adhesive 40a from sticking to other parts of the sanitary napkin 20 when the napkin is inwardly trifolded.

Examining the components of the sanitary napkin 20 in more detail with continuing reference to FIG. 1, the sanitary napkin 20 has a generally centered longitudinal centerline 36. As used herein the term "longitudinal" refers to an imaginary line, axis or direction of the sanitary napkin 20, which line, axis or direction is typically centered between the side margins of the napkin and is generally aligned with the vertical plane which bisects a standing wearer into left and right body halves. The terms "lateral" or "transverse" refer to an imaginary line, axis or direction generally orthogonal to the longitudinal direction and within the plane of the sanitary napkin 20, which is generally sideways aligned relative to the wearer.

The topsheet 22 is the component of the garment which is oriented towards and contacts the body of the wearer and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets 22 may be made from nonwoven materials and perforated polyolefinic films.

The topsheet 22 has a plurality of apertures to permit liquids deposited thereon to pass through to the core 26. Such apertures may, but need not, be present in the flaps 28. An apertured polyolefinic film topsheet 22 having about 5 to about 60 percent open area, typically about 25 percent open area, and a thickness of about 0.01 to about 0.05 millimeters prior to aperturing and about 0.46 to about 0.51 millimeters after aperturing is suitable.

If desired, the topsheet 22 may be treated with a surfactant to enhance fluid penetration to the core 26. The surfactant is typically nonionic and should be nonirritating to the skin. Suitable methods for treating the topsheet with a surfactant are described in U.S. Pat. Nos. 4,950,264 and 5,009,653, issued to Osborn. A suitable surfactant is sold by the Glyco Chemical, Inc. of Greenwich, Conn. as "PEGOSPERSE" 200 ML.

A particularly suitable topsheet 22 may be made in accordance with U.S. Pat. No. 4,342,314, issued Aug. 3, 1982 to Radel et al. and U.S. Pat. No. 4,463,045, issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Tredegar Film Products, formerly known as Ethyl Corporation, Visqueen Division, of Terre Haute, Ind. has been found to work well.

The backsheet 24 may be any flexible, liquid impervious or liquid resistant material, such as a polyolefinic film. The backsheet 24 prevents discharges collected by and contained in the sanitary napkin 20, particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness, preferably about 0.02 millimeters in thickness, has been found to work well. A polyethylene film, such as is sold by Tredegar Film Products under model XP-39385 has been found particularly well suited for this invention.

Further, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and an uniaxially elastically extensible elastomeric film such as described in U.S. Pat. No. 4,476,180 issued to Wnuk.

In one preferred embodiment, the backsheet 24 is slightly larger than the topsheet 22 and the absorbent core 26. In such an embodiment, the topsheet 22 and intermediate absorbent core 26 may be peripherally circumscribed by the backsheet 24 which has a radial margin of about 0.5 centimeters to about 1.5 centimeters, preferably about 1.0 centimeter, from the side margin of the topsheet 22. This geometry provides a marginal area of protection should the core 26 become overloaded or the sanitary napkin 20 otherwise fail. In such an embodiment the backsheet 24 and flaps 28 are preferably unitary and coextensive.

The backsheet 24 and the topsheet 22 are preferentially peripherally joined using known techniques, either entirely, so that the entire perimeter of the sanitary napkin 20 is circumscribed by such joining, or are partially peripherally joined. Any arrangement that provides for a unitary assembly and capture of the core 26 intermediate the topsheet 22 and backsheet 24 is suitable. Such an assembly has two mutually opposed major faces, one defined by the topsheet 22 and one defined by the backsheet 24.

The outwardly oriented face of the backsheet 24 preferably further comprises means 40 for attaching the sanitary napkin 20 to the undergarment of the wearer. Pressure sensitive adhesive 40a has been found to work well. Preferably a strip 40a of longitudinally oriented adhesive provides good protection against either the front or the back of the sanitary napkin 20 being detached from the wearer's undergarment. The strip 40a may be continuous or intermittent. A particularly preferred arrangement utilizes two longitudinally oriented strips 40a, one on each side of the longitudinal centerline 36.

The absorbent core 26 is the means for collecting and containing bodily discharges, particularly menses, deposited thereon or which otherwise traverse through the liquid permeable topsheet 22. The core 26 is the component of the sanitary napkin 20 which receives and retains the bodily discharges. The core 26 is conformable and nonirritating to the skin, and preferably relatively thin. The core 26 may be rectangular, hourglass shaped, or any other suitable shape. The core 26 preferably has two opposed faces, one oriented towards the backsheet 24 and one oriented towards the topsheet 22.

Suitable core 26 materials include, but are not limited to combinations of airfelt, such as cellulose wadding, and fibrated communition pulp; layers of tissue paper; and absorbent gelling materials. If a tissue paper core 26 is selected, the tissue paper may be made in accordance with U.S. Pat. No. 4,191,609, issued Mar. 4, 1980 to Trokhan, U.S. Pat. No. 4,529,480, issued to Trokhan on Jul. 16, 1985, and European Patent Application Publication Nos. WO 92/00414, WO 92/00415, and WO 92/00416, published Jan. 9, 1992.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

If it is desired to incorporate absorbent gelling materials into the core 26 of the sanitary napkin 20, absorbent gelling materials made in accordance with U.S. Pat. Re. No. 32,649, issued Apr. 19, 1988 to Brandt et al. are suitable. A suitable core 26 comprises a laminate of absorbent gelling materials and tissue may be purchased from the Grain Processing Corporation of Muscatine, Iowa under Model Number L535.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to en sure proper containment of bodily discharges. This arrangement also provides for a unitary assembly.

The core 26 is preferentially joined to the topsheet 22, and may be joined to the backsheet 24. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined relationship between the first member, or component, and the second member, or component, is intended to remain for the life of the sanitary napkin 20.

Joining may be accomplished by any suitable method, such as adhesively bonding the core 26 to the topsheet 22 or the backsheet 24. The adhesive (not shown) may be applied in any suitable spray pattern, such as a spiral, or in longitudinally oriented beads. The adhesive should be surfactant resistant and of low pressure sensitivity, so as not to stick to the skin of the wearer.

The sanitary napkin 20 preferably has a caliper of less than about 4 millimeters and more preferably less than about 2 millimeters, as measured with a comparator gauge having an approximately 80.0 gram test weight and an approximately 10.0 gram comparator foot having a diameter of about 2.54 centimeters and a contact surface area of approximately 5.1 square centimeters. Also, the sanitary napkin 20 preferably has a topsheet 22 surface area of at least about 100 square centimeters to prevent discharged fluids from missing the target area.

The sanitary napkin 20 may also comprise a flap 28 extending from a longitudinal side margin 30 of the sanitary napkin 20. Preferably, the sanitary napkin 20 has one flap 28 extending from each longitudinal side margin 30 of the sanitary napkin 20. The flaps 28 have a proximal end 44 which is typically coincident with the juncture of attachment of the flap 28 to the longitudinal side margin 30 of the sanitary napkin 20. Alternatively, the proximal end 44 of the flap 28 may be joined to the sanitary napkin 20 at another location, e.g., spaced enough from and juxtaposed with the longitudinal side margin 30.

The flaps 28 extend laterally outwardly from the sanitary napkin 20 and terminate at a distal end 46 which represents the portion of the flaps 28 furthest from the longitudinal side margins 30 of the sanitary napkin 20. The distal ends 46 of the flaps 28 are directed away from the longitudinal centerline 36 and central portion of the sanitary napkin 20. As used herein the phrase "central portion" refers to that part of the sanitary napkin 20 intermediate, particularly laterally intermediate, and defined by the proximal ends 44 of the flaps 28. The flaps 28 may be of any shape desired, with one preferred shape being shown in FIG. 1.

The flaps 28 may be comprised of an integral and contiguous extension of the topsheet 22, the backsheet 24, or a laminate of both 22 and 24. Alternatively, the flaps 28 may be made of a separate and independent piece of material joined to the longitudinal side margins 30 of the sanitary napkin 20. Each flap 28 has one face generally coextensive of the topsheet 22 and a mutually opposed face generally coextensive of the backsheet 24. A face of the flap 28 is considered to be coextensive of the topsheet 22 or the backsheet 24 if a line having a lateral component can be drawn from the topsheet 22 or the backsheet 24, respectively, which does not cross a portion of the side margins 30 or 32 at the perimeter of the central portion of the sanitary napkin 20, unless such portion of the side margins 30 or 32 is generally longitudinally adjacent the proximal end 44 of the flap 28.

The flaps 28 preferably have a means 40 for attaching one face of the flap 28 to the wearer's undergarment or to the other flap 28. The attachment means 40 may be a mechanical fastener or, preferably, pressure sensitive adhesive 40b. If pressure sensitive adhesive 40b is selected, it should be disposed on the face of the flap 28 generally coextensive of the backsheet 24 so that when the flaps 28 are wrapped around the crotch portion of the wearer's undergarment, the adhesive 40b will face the outside of the wearer's undergarment. A generally rectangular patch of adhesive 40b on each flap 28, about 25 millimeters×20 millimeters in size, works well. Suitable pressure sensitive adhesive 40 is sold by the Anchor Continental, Inc., 3 Sigma Division of Covington, Ohio as 0.02 millimeter pass with Century Adhesive A305-4.

For packaging, the flaps 28 are folded over the topsheet 22 so that the flaps 28 are in the topsheet facing relationship of FIG. 2. The flaps 28 are considered to be in a topsheet facing relationship if a line generally perpendicular to the plane of the sanitary napkin 20 drawn outwardly from the topsheet 22 intercepts either face of the flap 28. The flaps 28 are preferably folded about the proximal edge 44 so that maximum coverage of the topsheet 22 is obtained. This arrangement provides a larger area of the topsheet 22 covered by the flaps 28, particularly the area of the topsheet 22 which is generally registered with the wearer's vagina, so that a sanitary and clean appearance of this portion of the topsheet 22 is promoted. It is not necessary that the flaps 28 be folded about the proximal ends 44, that the flaps 28 be in contacting relationship with the topsheet 22, or that no other folds occur between the distal and proximal ends 44 and 46 of the flaps 28. It is only necessary that the flaps 28 face towards the topsheet 22 and discourage outside contamination from readily soiling the portion of the topsheet 22 covered by the flaps 28.

Folding the flaps 28 in the configuration of FIG. 2 exposes the patch 40b of adhesive on the face of the flaps 28 generally coextensive of the backsheet 24. To prevent contamination and blocking of this adhesive patch 40b, each flap 28 may be covered with a separate and dedicated piece of release liner 35'.

It will be apparent to one skilled in the art, however, that the flaps 28 may be folded over the backsheet 24 or, convolutely folded so that one flap 28 overlays the topsheet 22 and the other flap 28 overlays the backsheet 24. All such embodiments are within the spirit and scope of the claimed invention.

The releasable wrapper 34 has a perimeter defined by longitudinal edges 34c and lateral edges 34d. Preferably, the lateral edges of the releasable wrapper 34 are juxtaposed with the respective lateral side margins 32 of the sanitary napkin 20. This arrangement provides a releasable wrapper 34 having sufficient longitudinal extent to conceal and to protect the sanitary napkin 20 in the later described folded configurations.

The wrapper 34 has opposed faces. One face is an inwardly oriented face 34a. The inwardly oriented face of the wrapper 34 is oriented towards the adhesive 40 and the outwardly oriented face of the backsheet 24. The other face 34b is an outwardly oriented face. It is opposed to the inwardly oriented face and oriented away from the sanitary napkin 20.

Preferably, the inwardly oriented face is release coated, to facilitate easy and convenient manipulation of the releasable wrapper 34, and particularly separation from the adhesive 40. Silicone release coatings, as are well known in the art, have been found to work well. The releasable wrapper 34 may be zone coated with the release coating only in the areas of the adhesive 40a and 40b, or may be entirely release coated throughout the inwardly oriented face as desired.

The releasable wrapper 34 may be made of films, kraft paper, calendered paper, or other materials as are well known in the art without departure from the spirit and scope of the claimed invention. One suitable releasable wrapper 34 is made of machine glazed or machine finished paper having a basis weight of about $40.7 \times 10^{-3}$ kilograms per square meter (25 pounds per 3,000 square feet). The inwardly oriented face of the wrapper may be coated with a release coating such as silicone. Suitable release coated wrapper materials are marketed by Akrosil of Menasha, Wis. as "SILOX" 4R/O and Silox C1S.

The releasable wrapper 34 may be made of one or more sheets of material. The wrapper 34 may, for instance, comprise a two component arrangement comprising the wrapper 34 as described herein that is combined with a conventional release strip that covers the adhesive 40a attached to the inwardly oriented face of the wrapper 34. Preferably, however, the releasable wrapper 34 comprises a single sheet that both covers the adhesive 40a and serves as a package for the sanitary napkin 20.

With continuing reference to FIG. 2, it can be seen that in one embodiment, the releasable wrapper 34 wraps at least one, and preferably each, longitudinal side margin 30 of the sanitary napkin 20 in a C-fold 50. As used herein, a "C-fold" refers to the configuration of a component which is folded over itself to provide a double thickness and may have a foreign component interposed between the layers of the folded component. As illustrated in FIG. 2, it is preferred that the sanitary napkin 20 and releasable wrapper 34 be equivalently and symmetrically disposed and folded about the longitudinal centerline 36.

In the C-folded arrangement of FIG. 2, the entire backsheet 24 is covered by the releasable wrapper 34 and a portion of the topsheet 22 juxtaposed with the longitudinal side margins 30 are also covered by the releasable wrapper 34. As used herein, "releasable" refers to the condition where a first component may be separated from a second component at least once without causing destruction or undue distortion of either component.

The illustrated arrangement provides the advantage that one entire major face, particularly the face associated with the backsheet 24, is protected by the releasable wrapper 34. The longitudinal side margins 30 of the sanitary napkin 20 are likewise protected. Additionally a portion of the topsheet 22 is protected by the releasable wrapper 34. Further, in this arrangement no significant portion of the releasable wrapper 34 extends laterally outboard of the sanitary napkin 20, obviating the need for a bulky package, or a region of the releasable wrapper 34 to be dedicated for sealing of the package.

As illustrated in FIG. 3, the sanitary napkin 20 and releasable wrapper 34 may be folded about two spaced-apart laterally oriented fold lines. As used herein, the phrase "spaced-apart laterally oriented fold lines" refers to longitudinally offset lines, generally parallel the lateral direction, and about which the sanitary napkin 20 and releasable wrapper 34 are commonly folded.

Folding the sanitary napkin 20 about the spaced-apart laterally oriented fold lines produces a folded arrangement defining three trisections 51 and 52, a central trisection 51 intermediate and bounded by two outboard trisections 52. The outboard trisections 52 may be more specifically described as an inner-outboard trisection 52a and an outer-outboard trisection 52b, or more simply as the first and third trisections. The central trisection 51, thus, comprises the second trisection. As used herein, inner and outer outboard trisections 52 are described relative to the central trisection 51 when the sanitary napkin 20 and releasable wrapper 34 are in the folded arrangement of FIG. 4. The inner-outboard trisection 52a is generally adjacent the central trisection 51 and intermediate such central trisection 51 and the outer-outboard trisection 52b when folded. Conversely, the outer-outboard trisection 52b is relatively further from the central trisection 51 due to the interposition of inner-outboard trisection 52a.

In the folded arrangement of FIG. 4, the package defines two mutually opposed major surfaces, one defined by the outer-outboard trisection 52b, and one defined by the central trisection 51. The arrangement of FIG. 4 produces a sanitary napkin 20 having an e-fold with a releasable wrapper 34 having a corresponding e-fold. The releasable wrapper 34 is preferably of sufficient longitudinal dimension to overlie one outboard trisection 52 and the central trisection 51. More preferably, the releasable wrapper 34 is of sufficient longitudinal dimension to overlie all three trisections 51 and 52, so that no adhesive 40a is exposed.

Referring back to FIG. 1, the releasable wrapper 34 may further comprise a means for maintaining the sanitary napkin 20 and releasable wrapper 34 in the aforementioned folded arrangement. Suitable means for maintaining the folded arrangement include hook and loop mechanical fasteners, such as are sold under the trademark "VELCRO"; heat and/or pressure seals; and, adhesives in the form of tabs, or adhesive 54 juxtaposed with the longitudinal edge of the releasable wrapper 34.

The adhesive 54 may be placed on the longitudinal edge of the releasable wrapper which is folded over so that it overlays and faces outwardly from the topsheet 22. In one execution, the adhesive 54 may be applied to the outboard trisections 52 so that when the inner-outboard trisection 52a is folded over the central trisection 51 such trisections 51 and 52a are releasably affixed to each other and adhesive is juxtaposed with the outer-outboard trisection 52b so that it may be releasably affixed to the inner-outboard trisection 52a. Alternatively, the adhesive 54 may be applied to the central and outer-outboard trisections 51 and 52b.

The adhesive 54 may be applied in a continuous strip (as shown), in an intermittent strip, or may be a single spot. It is not critical which form the adhesive 54 is applied, only that it have sufficient peel strength to maintain the folded arrangement until it is desired to conveniently open the sanitary napkin 20 and releasable wrapper 34 for the first use by the wearer.

In one variation, the adhesive 54 may further comprise and be disposed on a tab 55 longitudinally extending beyond the lateral edge of the outer-outboard trisection 52b. The adhesive 54 of the tab 55 longitudinally beyond such lateral edge is affixed to the exposed face of the inner-outboard trisection 52a.

FIG. 4A shows one particularly preferred embodiment of an adhesive tab. The adhesive tab arrangement is referred to as a "tape sandwich". The tape sandwich comprises an adhesive tab 55 that is provided with a complementary landing member 57. The tab 55 and landing member 57 form a fastening system, such as adhesive fastening system 59. The fastening system 59 may be used to initially secure the package at the time of manufacture and maintain the package in a secured condition until it is opened by the consumer. The adhesive tab 55 may also be used to securely reclose the wrapper 34 and the used sanitary napkin 20 for disposal. For reclosing the package for disposal, it is preferable that the adhesive tab 55 be secured to a portion of the wrapper 34 that does not include a landing member.

The adhesive tab arrangement shown in FIG. 4A permits more aggressive adhesives to be used to attach the tape 55 to the wrapper 34 than are possible without such a construction. The tab arrangement shown in FIG. 4A can also be applied during manufacture to the package formed by the releasable wrapper 34 contemporaneously with its complementary landing member 57. Other advantages are described in greater detail below.

The component parts of the fastening system 59 include the tab 55, which preferably comprises a piece of tape. The tab or tape 55 comprises a first portion 61 and a second portion 63. The first and second portions 61 and 63 (and the subcomponents of these sections) can be arranged in several different manners. For instance, they can be separate components attached to the tab 55, etc. Preferably, however, the first and second portions 61 and 63 are contiguous segments of the tab 55.

The first portion 61 of the tape 55 is preferably permanently attached to a first surface during manufacture of the article(s) to which the tape sandwich is attached. The first portion 61, as a result, may also be referred to as a "manufacturer's end". In the embodiment shown in FIG. 4, the first surface 34' is a portion of wrapper 34 near the lateral (or end) edge of the third trisection 52*b*.

The second portion 63 of the tape 55 extends outward beyond the end of the first surface 34'. The second portion 63 serves at least two main purposes. The second portion 63 forms a releasable bond with the landing member 57 located on a second surface 34". The second portion 63 is also grasped by the consumer when it is desired to open and close the package. (That is, when the consumer desires to unfasten and refasten the two surfaces). The second portion 63, as a result, may also be referred to as a "tab portion", "user's portion", or "user's end".

The discussion of the fastening system 59 shown in FIG. 4A will employ the following convention for describing the respective surfaces or sides of its components. When the tab 55 is secured to close the package, the side of the components facing the package will be referred to as the "inner", "inside" (or inwardly-facing) surface. These will be designated by the reference number of the component together with the letter "a". The other side of the components will be referred to as the "outer", "outside" (or outwardly-facing) surface. These will be designated by the reference number of the component together with the letter "b". The ends of the components will be referred to by the reference number of the component together with the letters "c" and "d". With this in mind, the components of the fastening system 59 will now be looked at in greater detail.

The first portion 61 of tape 55 has a relatively strong (or aggressive) adhesive, first adhesive, 65 permanently bonded to its inside surface 61*a*. The first adhesive 65 is used to permanently attach the first portion 61 to the portion of the wrapper 34 near the lateral (or end) edge of the third trisection 52*b*. The term "permanently attach", as used herein, typically refers to a connection that cannot be unattached without at least partially destroying one of the attached components.

The second portion 63 of the tape 55 in the embodiment shown in FIG. 4A, comprises a number of sections. Some of these sections are optional. These include an optional first section or "spacer" (or "spacing section") 63' which has no adhesive on its inside surface 63'*a*. The spacer 63' provides an adhesive-less length of tape so the tape 55 will not stick to any portion of the wrapper 34 that is not covered by landing member 57 material. The spacer 63', thus, eliminates the possibility of unintentionally creating a permanent seal between the tape 55 and a second surface 34", such as the first trisection 52*a* of the wrapper 34.

The second portion 63 of the tape 55 further comprises a second section or fastening member 63". The fastening member 63" is the portion of the tape 55 which is releasably attached to the landing member 57. The fastening member 63" has an adhesive, second adhesive 67, permanently bonded to its inside surface 63"*a*. The fastening member 63" may, thus, be referred to as the "adhesive containing section". The second adhesive 67 is a relatively aggressive adhesive.

The second adhesive 67 is a more aggressive adhesive than could ordinarily be used to form a releasable bond between the tape 55 and the second surface 34" if the landing member 57 was not present. The second adhesive 67 can be sufficiently aggressive that it would form a permanent bond with the second surface 34", in the absence of the landing member 57. The upper limit on the strength of the second adhesive 67 is primarily determined by the release characteristics of the landing member 57. Preferably, for ease of manufacture, the second adhesive 67 is the same type adhesive used for the first adhesive 65.

The aggressive adhesives used as the second adhesive 67 preferably require relatively high peel forces as measured according to ASTM Std. D 3330M for Peel Adhesion of Pressure Sensitive Tape at 180 Degree Angle. For example, suitable aggressive adhesives for creating permanent bonds to plastic films typically require forces greater than about 20 to 25 oz. for separation. By way of comparison, adhesives that were typically used previously to create a releasable bond (i.e., without the tape sandwich) could be separated by forces less than about 10 to 20 oz. The ranges provided above are by way of example only. It is understood that the ranges applicable for a particular material are highly dependent on the substrate.

Suitable aggressive adhesives are manufactured by M & C Specialties Company of Southhampton, Pa. as product numbers 445 and 794, which are listed as being 30 oz. and 50 oz. adhesives, respectively.

The third section comprises a "tab end" at one end of the tape 55. The second portion 63 is, therefore, arranged so that the second section or fastening member 63" is between the first section or spacer and the tab end or third section 63'''. When the optional tab end 63''' is in the configuration shown in FIG. 4A, it preferably has no adhesive on its inside surface. The tab end 63''' of the tape 55 extends further outward from the lateral end of the releasable wrapper 34 and can be used by the consumer to peel the tape 55 away from the landing member 57.

The landing member 57 is any suitable element to which the fastening member 63" (on the tape 55) can be releasably attached by such aggressive adhesives. The landing member 57 can comprise any material with which such a releasable bond can be formed. Suitable materials include, but are not limited to tape, paper, film, and the like. These materials may be, and preferably are, release treated as described below. The landing member 57 has a surface area which is preferably at least as large as that of the second adhesive.

The landing member 57 shown in FIG. 4A comprises a tape, or landing tape. The landing member 57 has its own aggressive adhesive, such as third adhesive 69, on its inside surface 57*a*. The third adhesive 69 is used for permanently affixing the landing member 57 to a second surface 34", such as the exposed face of the first trisection 52*a*.

The outside surface 57*b* of the landing member is preferably treated with a material to make that surface releasable when contacted by the relatively aggressive adhesive on the second section 63" of the tape 55. The outside surface 57b can be treated by coating it with a "release material" 71. For instance, the outside surface can be coated with silicon, lacquers, or it can be treated in any manner known in the art for providing a releasable surface.

The tape sandwich with its complementary landing member 57 is thus, able to permit more aggressive adhesives to be used to attach the tape 55 to the wrapper 34. If the landing member 57 were not used, such more aggressive adhesives might tear the wrapper 34 upon opening the sealed package, particularly if a paper wrapper 34 is used. The tape sandwich arrangement is also advantageous because due to the use of the complementary landing member 57 it is not necessary to tailor the strength of the second adhesive 67 to the properties of the wrapper material. Previously, manufacturers had to attempt to find the narrow range of adhesive strengths that could be used for the wrapper 34 material which was both strong enough to seal the package but not so strong that it would destroy the package or the resealability upon opening. This required a compromise since this narrow range required the use of adhesives that were too weak to reliably form an adequate bond particularly for reclosing the package for disposal by the consumer. The fastening system of the present invention is not dependent on the characteristics of the wrapper, or other substrate. Thus, the same fastening system can be used to releasably attach the tape 55 to numerous different types of substrate surfaces regardless of their material strength and composition.

FIG. 4B is an alternative embodiment of the adhesive tab arrangement shown in FIG. 4A. In this embodiment, the tab end 63''' is adhesively coated and then folded over on itself and secured to form a folded end tab 72. The folded end tab 72 is easier for the user to grip. The tab in FIG. 4B has a second adhesive 67 that extends to the end 55d of the tape 55. The second adhesive 67 need not extend all the way to the end, however. The second adhesive 67 only needs to extend far enough that the tab 55 can be folded over and secured to itself.

FIG. 4C shows an embodiment in which the surface area of the landing tape 57 is larger than that of the second adhesive 67. This embodiment provides some room for error in aligning the second adhesive 67 and the landing member 57 during manufacture. It also provides room for error in aligning these two elements if the tape 55 and the landing member 57 are not contemporaneously affixed to the package during manufacture. FIG. 4C also illustrates an embodiment in which the area covered by the third adhesive 69 is less than the surface area of the landing member 57. It is thus, not necessary that the third adhesive 69 cover the entire inside surface 57a of the landing member 57.

FIG. 4D shows an alternative embodiment in which the landing tape 57 is not used. In FIG. 4D, the landing tape 57 is eliminated and the second surface 34" is coated with a release material 71. Suitable release materials include any of those described previously such as silicon coatings (e.g., "SILOX"), lacquers, etc. The second surface 34" is coated over the same area where the landing tape 57 could have been located. The coated second surface 34", thus, provides a "landing surface" 73.

FIG. 4E shows a variation of the embodiment of FIG. 4C. FIG. 4E shows a landing member 57 with a surface area that is much larger than the surface area of the second adhesive 67. More specifically, the landing member 57 is of such a size that it lies at least partially under the first surface 34'. In this case, the landing member 57 lies at least partially under the "flap" on the package formed by the wrapper 34. The advantage of this embodiment is that it eliminates the need for the first section or spacer 63'. This simplifies the construction of the tape 55. In lieu of providing a gap between the first and second adhesives, the first adhesive 65 can be applied over the entire inside surface 55a of the tape 55.

FIG. 4F shows an alternative embodiment that does not use a separate tape 55. FIG. 4F shows a wrapper 34 that has an adhesive 75 on the inside surface of its third trisection 52b. Like the adhesives in many of the embodiments described herein, the adhesive 75 could be applied in a patch, a strip, a single bead, etc. Preferably, in this embodiment, it is a single bead. A landing member 57 or landing surface 73 is provided beneath the adhesive. In this embodiment, the wrapper material 34 serves the function of the tape 55. This embodiment provides the advantage of allowing an aggressive adhesive to be used without the need for a separate tape 55.

FIG. 4G shows an alternative embodiment in which the tape 55 is eliminated. The second surface 34" has a landing member 57 affixed to it. The landing member 57 comprises a piece of two-sided or double-sided adhesive tape. The inside surface 57a of the double-sided tape is coated with an aggressive permanent adhesive 69. The aggressive adhesive 69 is used to permanently affix the double-sided tape to the second surface 34". The outside surface 57b of the tape 57 is coated with a release material 71. The outside surface 57b is then also coated with an aggressive adhesive 75. The aggressive adhesive 75 transfers to the first surface 34' and permanently affixes itself to the first surface 34' when the tape sandwich is brought in contact with the first surface 34. The aggressive adhesive detaches from the double-sided landing tape 57. The coated outside surface 57b of the landing tape 57, thus, provides a releasable fastening surface for securing the aggressive adhesive 75 on the inside surface of the first surface 34' to the landing tape 57.

There are numerous other variations of the embodiments shown in FIGS. 4A–4G. For instance, there could be more than one tab. In other variations, the relation ship between the various tape and adhesive components of the fastening system could be rearranged in a number of different ways. In other variations, alternative types of fastening devices known in the art could be used in these various combinations instead of adhesives. For instance, the landing member 57 and the fastening member 63 could comprise high static vinyl as is described in U.S. Pat. No. 4,979,613 issued to McLaughlin, et al. on Dec. 25, 1990.

The tab construction described herein could also be used on other types of packages. For instance, any of the embodiments described herein could be used on a package similar to that described in the McLaughlin patent and a sanitary napkin with a conventional release paper could be folded and inserted into such a package.

The tab construction could also be used on other articles, such as on diapers or other types of disposable absorbent articles. Suitable diapers are described in U.S. Pat. No. Re. 26,152, issued to Duncan, et al. on Jan. 31, 1967, U.S. Pat. No. 3,860,003, issued to Buell on Jan. 14, 1975, U.S. Pat. No. 4,909,803, issued to Aziz, et al. on Mar. 20, 1990, U.S. Pat. No. 4,695,278, issued to Lawson on Sep. 22, 1987, and U.S. Pat. No. 4,704,115, issued to Buell on Nov. 3, 1987. Fastening systems for absorbent articles that could either be replaced by fastening systems of the present invention, or that have certain features that could be combined with the fastening system of the present invention to yield new fastening systems are disclosed in U.S. Pat. No. 4,896,724, issued to Scripps on Sep. 26, 1989, U.S. Pat. No. 4,846,815, issued to Scripps on Jul. 11, 1989, U.S. Pat. No. 4,894,060, issued to Nestegard on Jan. 16, 1990, U.S. Pat. No. 4,946,527, issued to Battrell on Aug. 7, 1990, U.S. Pat. No. 3,848,594, issued to Buell on Nov. 19, 1974, U.S. Pat. No. 4,662,875, issued to Hirotsu, et al. on May 5, 1987, and U.S. Pat. No. 5,053,028, issued to Zoia, et al. on Oct. 1, 1991.

Figure 5:
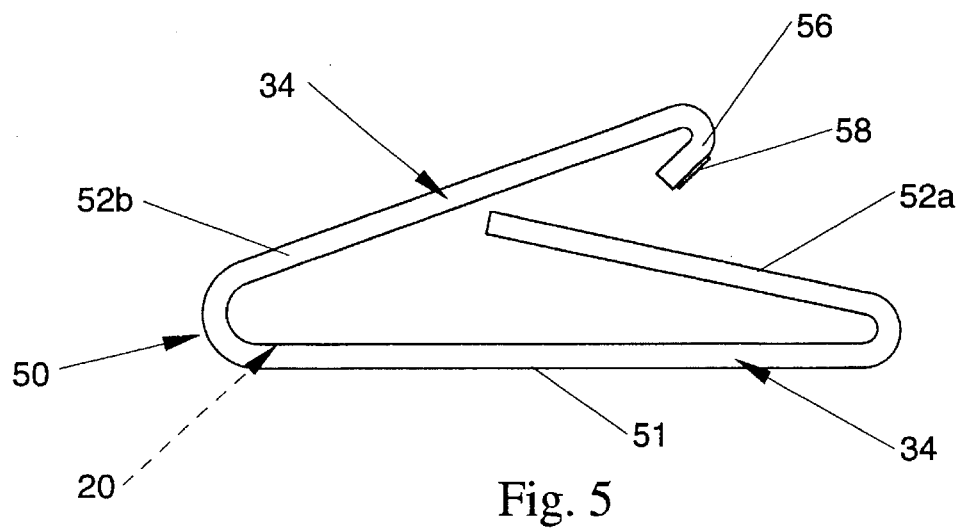
FIG. 5 is a profile vertical elevational view of a variant embodiment having the releasable wrapper folded over one lateral side margin of the sanitary napkin.

FIG. 5 illustrates a variant embodiment of the invention wherein the releasable wrapper 34 has a longitudinal extension 56 which overlays at least one, and if desired both, lateral side margins 32 of the sanitary napkin 20. This arrangement provides further protection for the sanitary napkin 20.

If only one longitudinal extension 56 is utilized, preferably, but not necessarily, it overlays the lateral side margin 32 of the outer-outboard trisection 52b. A means to maintain the sanitary napkin 20 and releasable wrapper 34 in the desired folded arrangement may also be advantageously employed with the longitudinal extension 56. In one particularly preferred arrangement, adhesive 58 is disposed on the longitudinal extension 56, particularly on the folded face of the longitudinal extension 56 which faces outwardly and away from the topsheet 22 when the sanitary napkin 20 is not in a folded arrangement and faces towards the opposed outboard trisection 52 when the sanitary napkin 20 and releasable wrapper 34 are folded.

The adhesive 58 may be juxtaposed with the longitudinal edges of the longitudinal extension 56, or generally coincide with the longitudinal centerline, or be positioned on the longitudinal extensions 56 generally coextensive of the longitudinal centerline 36. Using either arrangement, the longitudinal extension 56 of the releasable wrapper 34 is adhered to a portion of the releasable wrapper 34 which is longitudinally inboard of the lateral side margins 32 of the sanitary napkin 20.

Figure 6:
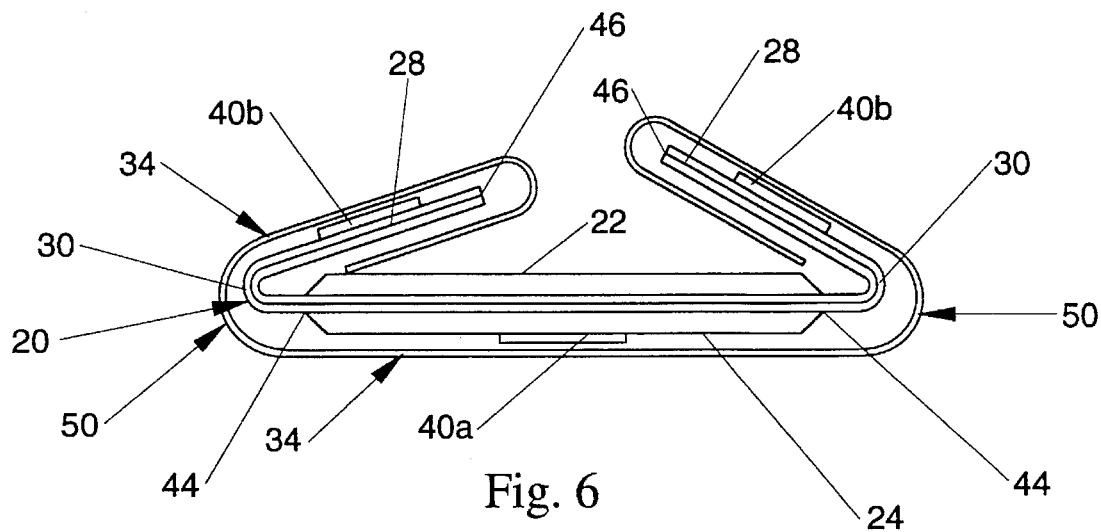
FIG. 6 is an endwise vertical elevational view of a releasable wrapper which encases both faces of the flaps of the sanitary napkin of FIG. 1.

FIG. 6 illustrates a variation which provides yet additional protection for a sanitary napkin 20 having flaps 28. In FIG. 6, the releasable wrapper 34, in addition to C-folding the longitudinal side margins 32 of the sanitary napkin 20, extends laterally inboard to the distal ends 46 of the flaps 28, and C-folds the distal end 46 of one, and preferably of both, flaps 28 of the sanitary napkin 20. The releasable wrapper 34 of such a configuration has a segment interposed between the flap 28 and the topsheet 22. Providing the releasable wrapper 34 extends longitudinally outboard of and between both lateral side margins 32, and the two C-folds 50 which overlay the distal ends 46 of the flaps 28 meet or overlap, the entire sanitary napkin 20 is protected by the releasable wrapper 34 without the necessity of trifolding about spaced apart laterally oriented fold lines.

FIGS. 7–9 generally illustrate embodiments where both flaps 28 of the sanitary napkin 20 are not folded over the same major face defined by the topsheet 22 and the backsheet 24. In the variations illustrated by FIGS. 7–9, the sanitary napkins 20 have one flap 28 folded over the topsheet 22, and the other flap 28 folded over the backsheet 24 in a convolute fold pattern.

At least one, and preferably both, flaps 28 of the sanitary napkins 20 of FIG. 7–9 have adhesive 40b associated with, and preferably joined to, the face of the flaps 28 which is generally coextensive of the backsheet 24. The flap 28 folded over the topsheet 22 will have the adhesive 40b of the flap 28 facing outwardly, where this adhesive 40b may be covered and protected by the releasable wrapper 34. If the flap 28 folded over the backsheet 24 also has adhesive 40b, such adhesive 40b is preferably covered by an independent piece of release paper (not shown). However, the flap 28 having adhesive 40b exposed by the selected convolute fold arrangement, may advantageously use the releasable wrapper 34 to cover such adhesive 40b, and, as well, cover the adhesive 40a associated with the central portion of the backsheet 24.

In the embodiment of FIG. 7, the one flap 28 of the sanitary napkin 20 has its distal end 46 wrapped in a C-fold 50 by the releasable wrapper 34. The corresponding first longitudinal side margin 30 of the sanitary napkin 20 is wrapped in a second C-fold 50. The remainder of the releasable wrapper 34 laterally extends across the sanitary napkin 20, covers the other flap 28, wraps the opposite longitudinal side margin 30 in a third C-fold 50 and extends laterally inwardly towards the longitudinal centerline, to approach the distal end 46 of the flap 28 of the first longitudinal side margin 30. If desired, the longitudinal edge of the releasable wrapper 34 which approaches the distal end 46 of such first flap 28 may overlap the portion of the releasable wrapper 34 which C-folds the distal end 46 of the flap 28.

It is to be understood by one skilled in the art that the first C-fold 50 of the releasable wrapper 34, which wraps the distal end 46 of the one flap 28, need not have its apex close to the distal end 46 (as illustrated), but rather this apex may be laterally displaced therefrom towards the opposite longitudinal side margin 30. As the apex of the C-fold 50 which wraps the distal end 46 of the one flap 28 approaches the opposite longitudinal side margin 30, a greater portion of the major face which such flap 28 overlays is covered and protected by a double thickness of the releasable wrapper 34. If desired, the releasable wrapper 34 of such a variant may be generally coterminous with, or laterally outboard of, such opposite longitudinal side margin 30 rather than be disposed laterally inboard of such opposite longitudinal side margin 30 as illustrated.

In the variation of FIG. 8, the releasable wrapper 34 has a first C-fold 50 wrapping the distal end 46 of either flap 28, wraps the corresponding longitudinal side margin 30 of the sanitary napkin 20 in a second C-fold 50. The releasable wrapper 34 extends generally uninterrupted across a major face of the sanitary napkin 20, particularly the major face opposite that which the C-folded flap 28 is folded.

The lateral edge of the releasable wrapper 34 may be generally coextensive with the other longitudinal side margin 30 (as illustrated). It will be recognized that the backsheet 24 may have adhesive 40a covered by an independent release paper (not shown) or may have such adhesive 40a adhered to the inwardly oriented face of the wrapper 34 (as illustrated). Furthermore, the apex of the first C-fold 50 which wraps the distal end 46 of the flap 28 may be adjacent such distal end 46 rather than adjacent the opposite longitudinal side margin 30, or may be at any intermediate position. If a major face of the sanitary napkin is exposed, as not illustrated by FIG. 8, preferably the exposed face is that face defined by the backsheet 24, so that the topsheet 22 is protected and remains in a sanitary condition.

FIG. 9 illustrates a releasable wrapper 34 which wraps one longitudinal side margin 30 of the sanitary napkin 20 in a C-fold 50 and covers the flap 28 corresponding to this longitudinal side margin 30. It is to be understood by one skilled in the art that the other longitudinal side margin 30 could be wrapped in a C-fold 50 as well, by an extension of the portion of the releasable wrapper 34 which covers such flap 28. A longitudinal edge of the releasable wrapper 34 is interposed between the other flap 28 and the major surface which the other flap 28 overlays.

In yet a further variation (not shown), the sanitary napkin 20 is folded in an S-fold about two spaced-apart transversely oriented fold lines, so that the topsheet 22 of one outboard trisection 52 faces outwardly and is exposed, and the backsheet 24 of the other outboard trisection 52 faces outwardly and is exposed. In an S-folded configuration, the releasable wrapper 34 may be somewhat shorter than the unfolded longitudinal dimension of the sanitary napkin 20, providing the releasable wrapper 34 is applied to the sanitary napkin 20 after it is S-folded.

With an S-folded sanitary napkin 20, the releasable wrapper 34 may overlay the trisection 52 which has the exposed topsheet 22, so that the topsheet 22 is completely covered, and wrap the longitudinal side margins 30 of the sanitary napkin 20 in C-folds 50. The longitudinal edges of the releasable wrapper 34 then overlay the backsheet 24 of the other exposed trisection 52. A feature common to this and any of the foregoing embodiments is that the longitudinal edges of the releasable wrapper 34 may be spaced apart, abut, or overlap as desired.

If desired, the S-folded sanitary napkin 20 may be rotated 90 degrees relative to the releasable wrapper 34, so that the longitudinal axes of the sanitary napkin 20 and the releasable wrapper 34 are mutually orthogonal. The S-folded sanitary napkin 20 is placed on the releasable wrapper 34 so that the trisection 52 of the sanitary napkin 20 having the exposed topsheet 22 is completely covered. One apex of the S-fold and a lateral side margin 32 is then wrapped by the releasable wrapper 34 in a C-fold 50. In this arrangement, the longitudinal edges of the releasable wrapper 34 bound the exposed backsheet 24 as described above. It will be apparent that this arrangement may be transposed, so that the releasable wrapper 34 overlays the topsheet 22 and the longitudinal edges of the releasable wrapper 34 overlay the backsheet 24.

With each of the S-folded sanitary napkin embodiments, the releasable wrapper 34 does not conform to a similar S-fold, but rather is generally U-shaped. This produces a somewhat shorter releasable wrapper 34 because the central trisection 51 of the sanitary napkin 20 does not have a dedicated length of releasable wrapper 34.

Figure 10:
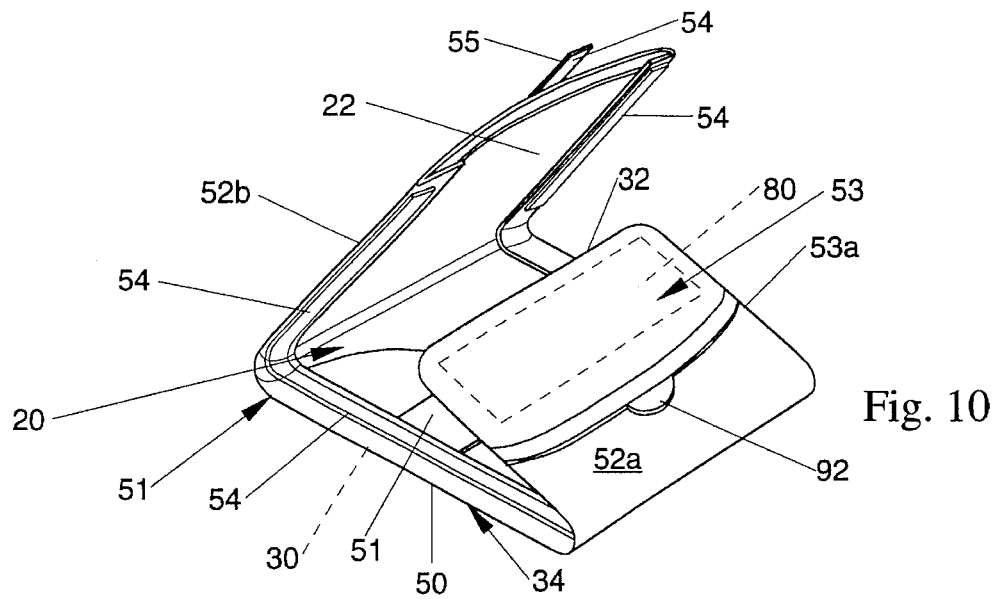
FIGS. 10–12 are perspective views of the sanitary napkin similar to FIG. 3 which show possible locations for a flap (or pouch) feature on the releasable wrapper.
Figure 11:
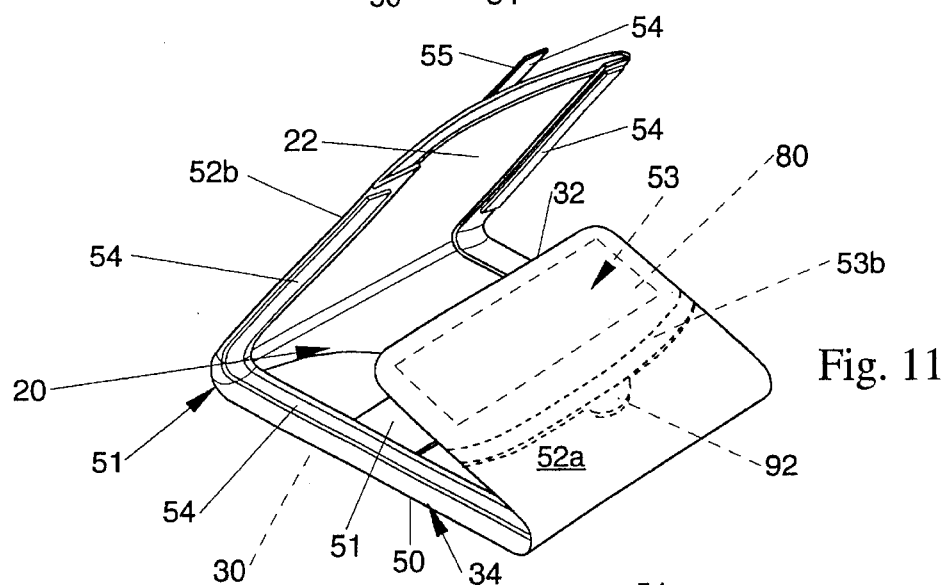
Figure 12:
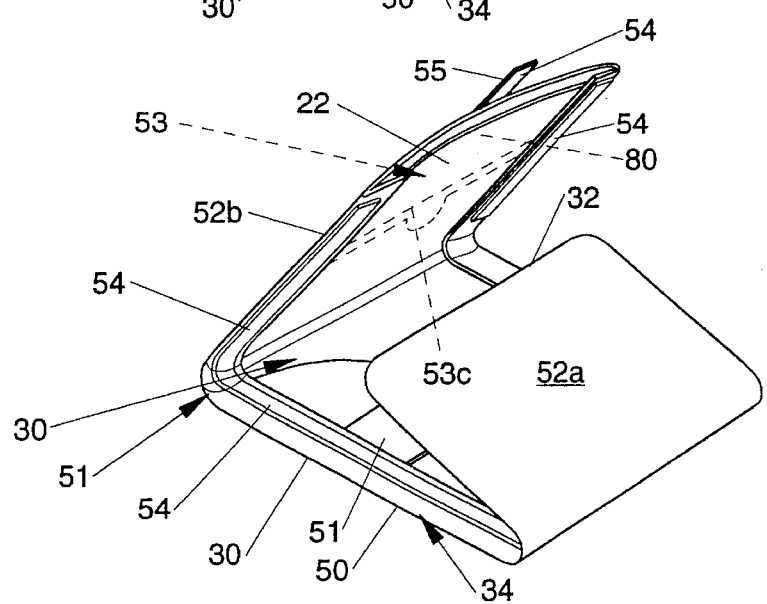

The releasable wrapper 34 (as shown in FIGS. 10–12) may also comprise a flap (or pouch) 53 to contain a cleansing wipe as described below, and/or to assist in the disposal of the sanitary napkin 20 and/or the cleansing wipe 80. A suitable flap (or pouch) is described in U.S. Pat. No. 4,556,146, issued to Swanson, et al.

The flap 53 can be used with releasable wrapper 34 embodiments that are configured to wrap the longitudinal side margins of the sanitary napkin in a C-fold (such as those shown in the drawings).

In other embodiments, the flap 53 can be used with releasable wrappers 34 that are configured to overlay only one major surface of the sanitary napkin 20 (i.e., not configured to wrap the longitudinal side margins of the sanitary napkin). In other alternative embodiments, the flap (and/or any other feature described in the Swanson, et al. patent or described herein could be used with releasable wrappers 34 that are not configured to wrap the longitudinal side margins of the sanitary napkin, and/or are also only folded about a single transverse axis. In other alternative embodiments, the releasable wrapper 34 and sanitary napkin 20 may be unfolded, or folded about two or more transverse axes. Instill other alternative embodiments, the flap or pouch may be provided on a completely different type of wrapper or package.

There are numerous possible locations on the releasable wrapper 34 for such a flap 53. The flap 53 can be located on either face of the wrapper, the inwardly oriented face of the wrapper 34, or the outwardly oriented face. The flap 53 is typically located on central trisection 51 on the outwardly oriented force of the wrapper 34, or at one of the ends of the wrapper 34. The flap 53 could, thus, alternatively, or additionally be located at the end of the inner-outboard trisection 52a, or at the end of the outer-outboard trisection 52b.

Figure 12A:
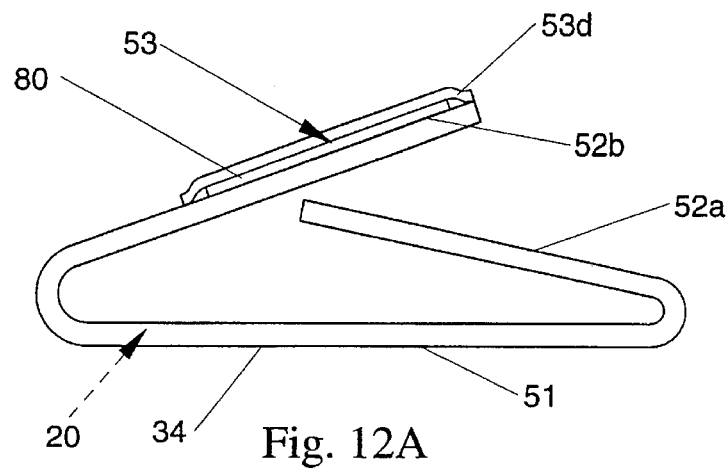
FIGS. 12A and B are profile schematic sectional views which show additional possible locatings for a flap (or pouch) containing a cleansing wipe.
Figure 12B:
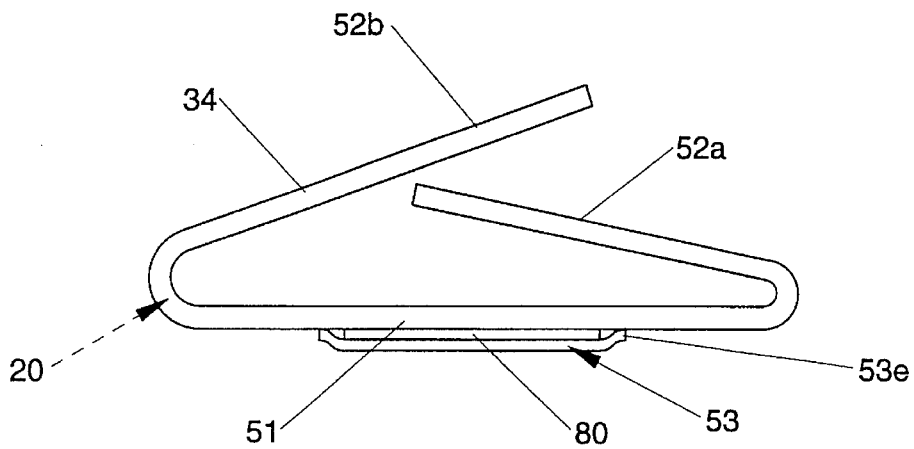

FIGS. 10–12B show five of the possible locations for the flap 53. These are designated 53a–53e. The flap in FIG. 10 designated 53a is located at the end of the inner outboard trisection 52a. The flap 53a in FIG. 10 is located on the outwardly oriented face of the wrapper 34. The flap in FIG. 11 designated 53b is located on the inwardly oriented face of the same trisection. The flap in FIG. 12 designated 53c is located on the inwardly oriented face of the outer outboard trisection 52b. The position of the flap 53 may be chosen (as described below) to provide more options for wrapping the used sanitary napkin for disposal. The flap in FIG. 12A designated 53d is located on the outwardly oriented face of the outer-outboard trisection 52b. The flap in FIG. 12B designated 53e is located on the outwardly oriented face of the central trisection 51.

The sanitary napkin 20 can be configured for disposal in at least three different ways using the wrapper 34. The user can roll up the used sanitary napkin 20, and insert it in the pouch (that is, under the flap 53). The remainder of the releasable wrapper 34 can then be folded, rolled, wrapped, etc. around the portion of the pouch 53 containing the sanitary napkin 20. If the releasable wrapper 34 is provided with a tape tab 55, in such a case, the tape tab 55 can be used to secure the releasable wrapper in a folded or rolled up configuration.

Alternatively, the sanitary napkin can be folded or rolled up and placed on the end of the releasable wrapper 34 opposite the end containing the flap. The sanitary napkin can then be rolled up in the wrapper 34. The flap 53 can then be pulled over the rolled up portion of the releasable wrapper 34 to secure the package in a rolled up configuration.

Alternatively, if in the previous alternative the flap 53 is on the opposite side of the releasable wrapper that the sanitary napkin is placed on and rolled up in, the flap 53 can be turned inside out and pulled over the rolled up sanitary napkin 20 to secure the package.

The alternative location for the flap designated 53b is an especially preferred embodiment for use in disposing a used sanitary napkin because it allows the sanitary napkin 20 to be configured for disposal in all three alternative ways. The other two alternative locations for the flap 53 are not as suitable if the user chooses the alternative of placing the sanitary napkin under the flap 53 and desires to roll up the sanitary napkin 20 and fasten the rolled up sanitary napkin in a rolled up configuration with the adhesive tab 55.

The sanitary napkin 20 of the present invention is packaged with a cleansing wipe 80.

The cleansing wipe 80 is a hygenic wipe that may be used by the wearer to clean menses and/or other body exudates from her body.

The cleaning of menses is particularly important because when menses leaves the wearer's body, it tends to smear over the pudendal region of the wearer's body and be retained on the wearer's skin and pubic hair. Furthermore, the menses often dries on the skin and in the pubic hair. This makes later cleansing difficult.

The inclusion of a cleansing wipe with the individual sanitary napkin provides several advantages. The wipe provides for physical cleansing. This increases physical comfort as well as psychological comfort by providing a feeling of cleanliness. The wipe may also be used to reduce soiling of the wearer's panties. One mechanism that causes panty soiling is the transfer of menses from soiled body surfaces to the wearer's panties. In addition, the use of the wipe may also provide a reduction in the odor associated with menstruation.

The cleansing wipe 80 is preferably a wet wipe (that is, liquid-containing) that is provided with an aqueous-based solution. The wipe 80 is preferably comprised of a nonwoven fabric impregnated with an aqueous cleaning mixture. The nonwoven fabric may be comprised of synthetic fibers or natural fibers (such as cellulose). The wipe 80 can, for instance, be made of a nonwoven material similar to toilet tissue or facial tissue. Less preferred embodiments might include dry wipes or wipes containing non-aqueous cleaning solutions such as mineral oils, and the emollient described in U.S. Pat. No. 4,481,243, issued to Allen on Nov. 6, 1984.

The cleaning mixture may include surfactants, alcohols, perfumes, antimicrobial agents, and pH buffers. The wipe 80 may also contain substances such as silicones that tend to inhibit menses from adhering to the wearer's skin and pubic hair. The cleaning mixture may also contain skin conditioning substances similar to those used in hand lotions, or any other substances known in the art for inclusion in cleansing wipes.

The cleansing wipe 80 is preferably both capable of being flushed in a toilet (i.e., it is "flushable"), and disintegrates sufficiently when flushed in a toilet and when being transported in the sewer system so it does not plug any element of a sewer system. In preferred embodiments, any wrapping material associated with the wipe is also flushable and disintegrates. Wrapping materials that meet such criteria include, but are not limited to silicone-treated polyvinyl alcohol films, or films coated with a polyvinyl alcohol, tissue coated or impregnated with polyvinyl alcohol, or similar or other water soluble materials. One material that may be suitable for use as both a cleansing wipe, and as a wrapping for the same is the hydro-entangled fabric described in U.S. Pat. No. 4,755,421, issued to Manning, et al. on Jul. 5, 1988.

The size of the cleansing wipe 80 can vary. The cleansing wipe 80 is preferably greater than or equal to about 4 square inches (about 25 square centimeters), and more preferably, is greater than or equal to about 9 square inches (about 50 square centimeters) in size. Preferably, the cleansing wipe 80 is less than or equal to about 225 square inches (about 1,450 square centimeters) in size. Even more preferably, the cleansing wipe 80 is between about 16 square inches (about 100 square centimeters) and about 50 square inches (about 320 square centimeters) in size. Most preferably, the wipe 80 is about 35 square inches (about 225 square centimeters) in size.

The drawing figures show several non-limiting alternative ways of packaging the cleansing wipe 80 with the releasable wrapper 34.

FIGS. 10–13 show an individually packaged wipe 80 that is included within the flap 53 of the releasable wrapper 34 and sealed. FIGS. 10–12B show that the wipe 80 can be packaged in flaps 53 located on various different portions of the releasable wrapper 34. The embodiments shown in FIGS. 10, 12A, and 12B may be preferred in cases in which it is desirable to remove the cleansing wipe 80 with minimal disruption of the portion of the package containing the sanitary napkin 20.

Figure 13:
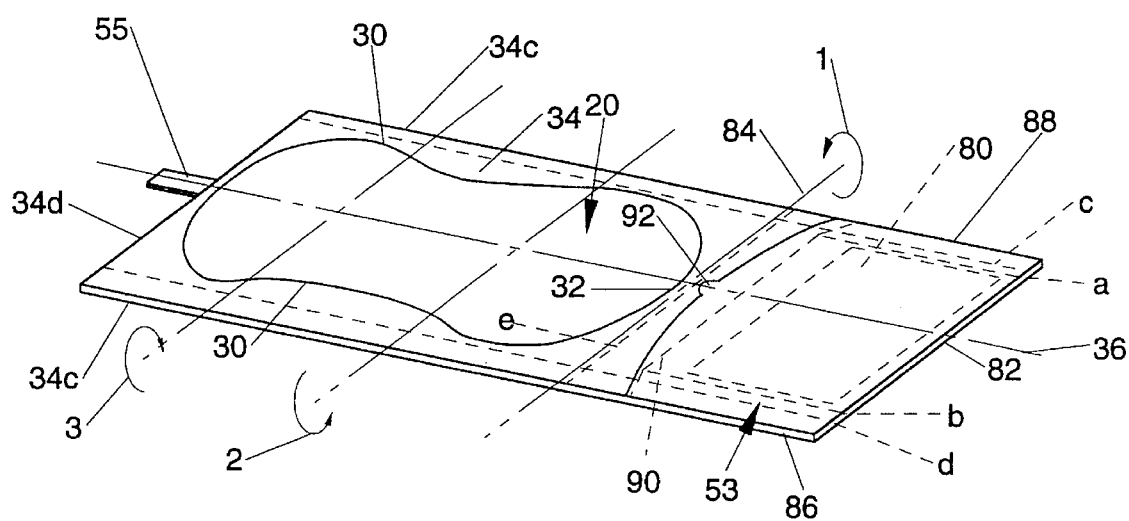
FIG. 13 is a simplified perspective view of a particularly preferred releasable wrapper for packaging a cleansing wipe.

FIG. 13 shows a particularly preferred releasable wrapper 34 for use in packaging the cleansing wipe 80. FIG. 13 shows that the releasable wrapper 34 extends beyond (at least) one end edge 32 of the sanitary napkin. In addition, the longitudinal edges 34c of the releasable wrapper 34 extend beyond the longitudinal side margins 30 of the sanitary napkin 20. The longitudinal edges 34c of the releasable wrapper are preferably not folded inward toward the sanitary napkin 20 in this embodiment, but in other embodiments they may be folded inward.

The flap 53 of the wrapper 34 shown in FIG. 13 has a preferred configuration. The folded wipe 80 is preferably placed on top of the releasable wrapper 34 as shown before the flap 53 is formed, for ease of manufacture.

The flap 53 may be formed by folding the end of the releasable wrapper 34 that extends beyond the end edge 32a of the sanitary napkin over the adjacent section of the releasable wrapper 34 to sandwich the wipe 80 therebetween. The releasable wrapper 34 is preferably folded so that, after folding, the folded section that forms the flap 53 covers the wipe 80 but does not cover the sanitary napkin. The flap 53, thus, still extends beyond one end edge 32 of the sanitary napkin 20.

In other alternative embodiments, the flap 53 may be a separate piece of material that is attached to the releasable wrapper 34. The same applies to any of the embodiments described herein which have flaps.

FIG. 13 shows that the folding closes one side 82 of flap or pouch 53 formed on the releasable wrapper 34. The mouth 84 of the flap 53 is then sealed with a releasable (or "openable") seal 90. The side edges 86 and 88 of the flap 53 are sealed with a liquid impermeable seal along dotted lines a and b. This sealing, thus, forms a four-sided sealed pouch for the cleansing wipe 80.

The releasable wrapper 34 containing the cleansing wipe 80 and sanitary napkin 20 are then preferably folded about transverse axes 1, 2, and 3. The folded package may be frangibly sealed outboard of the liquid impermeable sealing line (c and d) along dotted lines a and b in accordance with the teachings of U.S. Pat. No. 4,556,146, issued to Swanson, et al. The folded package may then be retained in its folded configuration with tape 55.

The seals around all sides of the pouch 53 must be sufficient to prevent substantial evaporation of the aqueous solution from the time the product is manufactured to the time it is used by the consumer. Any number of sealing mechanisms may be used, including, but not limited to heat and/or pressure seals, ultrasonic seals, glue seals, and zippered track sealing systems such as Dow Company's "ZIP LOCKS". In addition, the pouch 53 may be lined with foil, or some other suitable material to further reduce evaporation.

The mouth 84 of the pouch 53 preferably has a convex shape with respect to the folded end 82 of the pouch when seen in plan view. This is particularly useful in providing for ease of opening the pouch 53, particularly when the pouch 53 is formed of extremely thin and flexible materials and the seal follows the shape of the mouth 84 of the pouch for the reasons described below. In other embodiments, the pouch 53 and its mouth 84 may be of any other suitable shape.

The pouch 53 must include a releasable seal for unsealing (or opening) the pouch 53 in order to remove the wipe 80. The releasable seal 90 may be at the mouth 84 of the pouch 53, i.e. at least a portion of the seals around all sides of the pouch is releasable or at some other portion of the pouch 53. The releasable seal 90 may comprise any suitable type of releasable seal, including, but not limited to releasable adhesives, releasable heat and/or pressure seals, perforations, rupture seals, tear seals.

The shape of the seal 90 may also be important, particularly if a releasable adhesive seal is used. Having a rounded adhesive for the releasable seal is highly preferred. The "rounded" releasable seal 90 preferably follows the plan view shape of the mouth 84 of the pouch 53. (That is, both have a convex configuration.) The rounded releasable seal 90 has the advantage that peeling forces applied to open the pouch 53 need only be initially exerted on a portion of the total area covered by the releasable adhesive. The releasable adhesive configuration provides the strength of a linear seal, but ease of opening so there will be less chance of tearing the pouch material.

The releasable seal 90 can be in other shapes that will provided a benefit similar to that of a rounded seal. Any seal shape that is configured so that portions (or segments) of the adhesive adjacent the openable edge of the pouch are closer to the openable edge than the remaining portions or segments of the adhesive will work. Seals meeting this criteria will also provide an easier opening pouch by permitting gradual peeling. An example of such a seal is the V-shaped seal shown in FIG. 13A. The V-shaped seal shown in FIG. 13A has a centerline that coincides with the longitudinal centerline 36.

The pouch 53 may also have a mechanism for assisting the user in opening the pouch 53, such as the tab 92 shown in FIGS. 10–13.

As noted above, the tape 55 may be used to retain the package in its folded configuration. In alternative embodiments, the tape 55 may not be used for holding the package initially, and may be preserved only for folding or rolling up and retaining the napkin and releasable wrapper 34 when disposing of a used sanitary napkin.

There are a non-limiting number of ways to preserve the tape 55 for use in sealing the package for use in disposal of a used sanitary napkin. In the following embodiments, the tape 55 is not used to seal the package prior to use of the sanitary napkin 20.

In one alternative embodiment, the exposed adhesive on the tape 55 can be covered with a release paper. The release paper can be removed, and the tape 55 can be used for disposal.

In another alternative embodiment, when the sanitary napkin is packaged, the exposed adhesive-containing section of tape 55 may be coated with a suitable release coating and folded over on itself in a manner similar to that used on diaper tapes. The tape 55 can than be unfolded and adhered to the package for disposal.

In another alternative embodiment, the tape 55 can be a removable tape. The removable tape can be fastened to the releasable wrapper 34 in such a manner that it does not retain the sanitary napkin in its folded configuration prior to use. For instance, the tape 55 can simply be disposed on a release coated portion of the releasable wrapper 34. The sanitary napkin can be placed in the wrapper 34 and the wrapper containing the sanitary napkin can then be folded or rolled into a package configured for disposal. The removable tape 55 can then be removed from the package and used to secure the package in its disposal configuration.

The releasable wrapper 34 shown in FIG. 13 can be provided with an optional perforation line at the place designated e. This will allow the user to tear off the pouch 53 containing the cleansing wipe 80. The user can then carry the pouch 53 as a separate package. In other embodiments, any other suitable means for releasably affixing the pouch 53 to the remainder of the releasable wrapper can be used instead of a perforation line.

FIGS. 13A–E show a method of folding a variation of the embodiment shown in FIG. 13.

The sanitary napkin 20 shown in these figures has side flaps 28 extending from each longitudinal side margin 30 of the sanitary napkin 20. The flaps 28 are folded over the topsheet 22 in a topsheet-facing relation ship. The pressure sensitive adhesive patches 40b on the flaps 28 are bridged by a single unitary release strip 35.

Figure 13A:
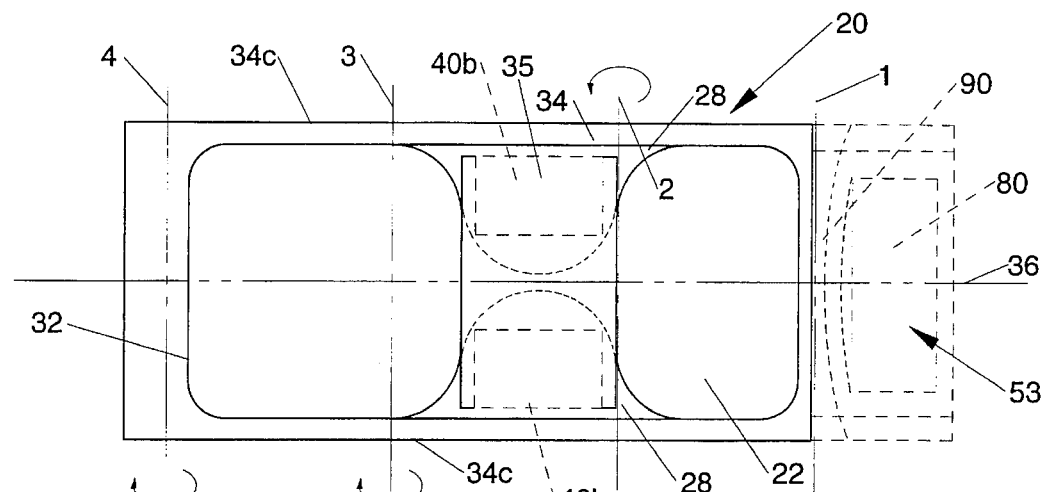
FIGS. 13A–E are plan views showing the folding of a variation of the embodiment shown in FIG. 13.
Figure 13B:
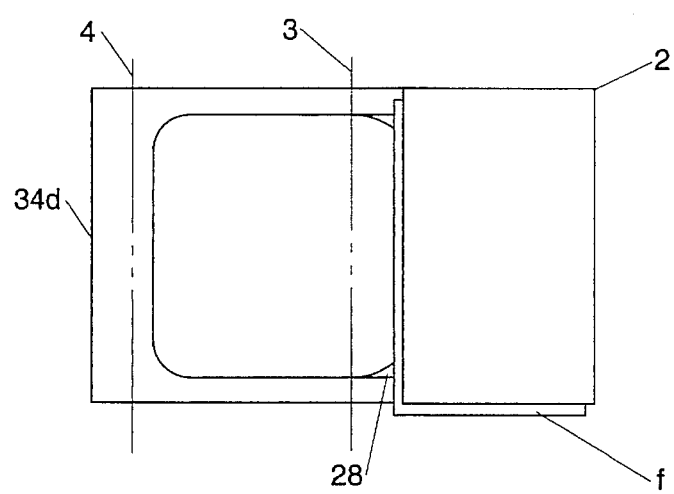
Figures 13C, 13D, 13E:
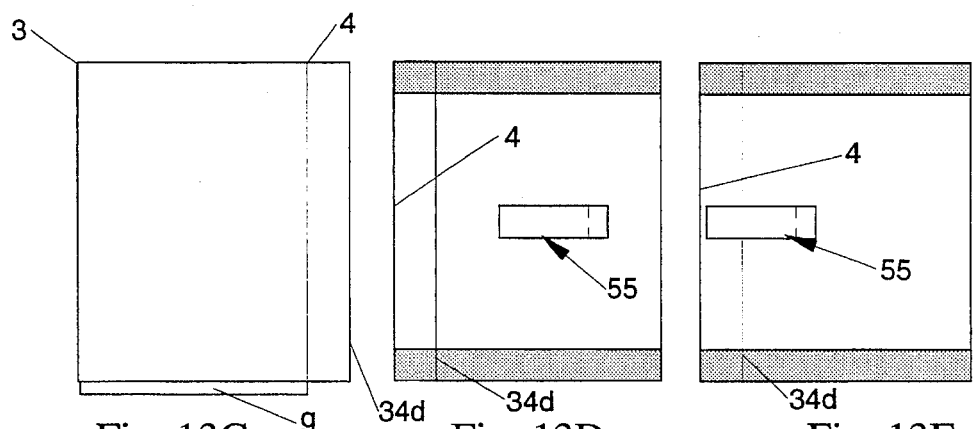

FIGS. 13A–C show that after the pouch 53 is formed with the cleansing wipe 80 inside, the releasable wrapper 34 is folded about the axes designated 1, 2, and 3 similarly to the embodiment shown in FIG. 13. The folding can be accomplished in any suitable way, such as by the use of folding boards f and g shown in FIGS. 13B and 13C.

The embodiment shown in FIGS. 13A–F differs, however, in that the end 34d of the releasable wrapper 34 (i.e., a second end) which is opposite the end containing the pouch 53 (i.e., the first end) also extends beyond an end edge of the sanitary napkin. This second end 34d of the releasable wrapper 34 extends beyond an edge 32 of the sanitary napkin 20. More specifically, second end 34d of the releasable wrapper extends far enough beyond the end edge 32 of the sanitary napkin 20 that it can be folded about a fourth fold axis, 4. This end 34d of the releasable wrapper can be wrapped from one side of the folded package 34e and fastened to the other side 34f.

Figure 13F:
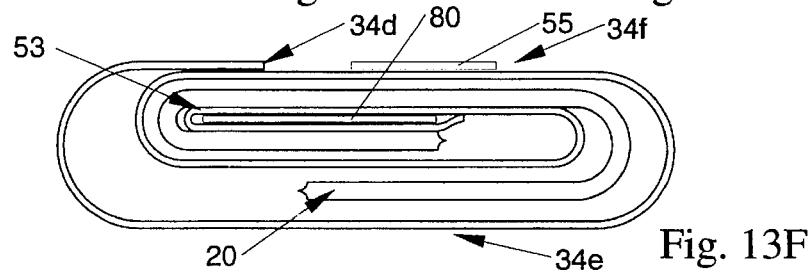
FIG. 13F is a side sectional view of the folded package shown in FIG. 13D.

The second end 34d of the releasable wrapper 34 can be fastened down by frangible sealing lines along the longitudinal edges 34c of the releasable wrapper package. In addition, as shown in FIGS. 13D and 13E, the releasable wrapper package can be provided with a tape 55. FIG. 13D shows an embodiment in which the tape 55 is preserved for use in securing the wrapper when disposing of a used sanitary napkin. FIG. 13E shows an embodiment in which the tape 55 is used in addition to the frangible seals to secure the second end 34d of the releasable wrapper 34 to the package. FIG. 13F is a sectional view of the package shown in FIG. 13D.

The variation shown in FIGS. 13A–F is advantageous because it provides additional protection for keeping the sanitary napkin 20 free from soiling prior to use. The folding of the second end 34d of the wrapper around the wrapper package closes off the package. This construction prevents pencils, pens, and other objects in the user's purse from marking and soiling the sanitary napkin 20.

The variation shown in FIGS. 13A–F is also particularly advantageous when used with thick sanitary napkins. Thick sanitary napkins tend to unfold after they have been wrapped. The wrapping of the second end 34d of the wrapper around the wrapper package reduces the tendency for thick sanitary napkins to unfold.

Many other variations of the versions of the package shown in FIGS. 13A–F are possible. In other versions of the package shown in FIGS. 13A–F, the pouch 53 could be on some other portion of the package. Instill other versions, the wipe 80 could be in a separate receptacle. For instance, in this latter case, the releasable wrapper 34 could be cut along the axis designated 1, and the wrapper 34 could have a separate receptacle attached to it after the wrapper is in its folded configuration. Alternatively, such a wrapper could be used simply to wrap the sanitary napkin by serving the advantages discussed above without a receptacle and a cleansing wipe.

Figure 14:
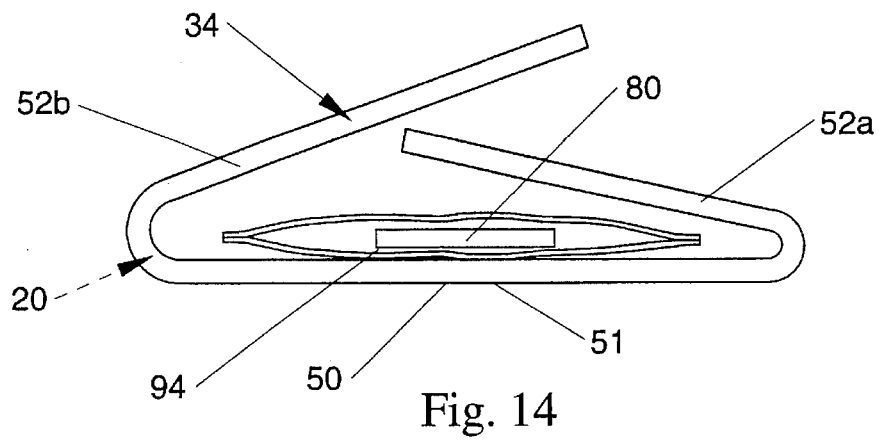
FIGS. 14 and 15 are profile schematic sectional views which show alternative placements for an individually packaged wipe.
Figure 15:
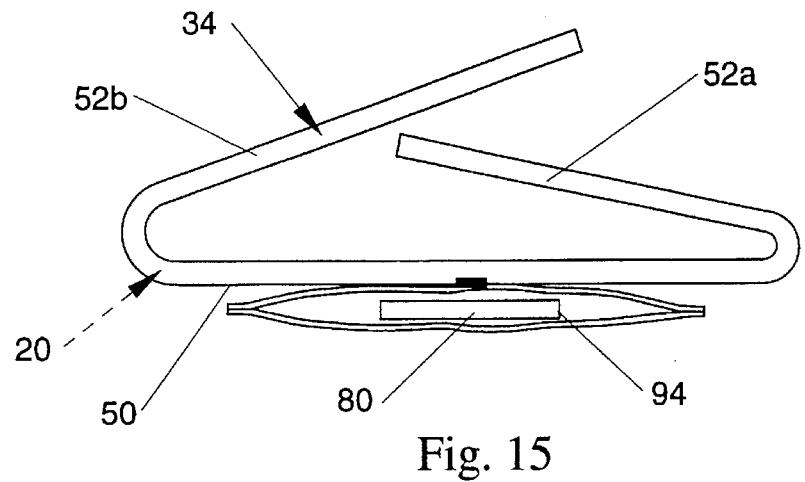

In the embodiments shown in FIGS. 14 and 15, rather than being inserted in a flap or pouch 53 provided on the releasable wrapper 34, the wipe 80 may be folded and sealed in a separate pouch, wrapping material, or other receptacle associated with the releasable wrapper 34.

FIGS. 14 and 15 show an individually packaged wipe 80 that is in a separate receptacle 94. The wipe 80 may be placed in a receptacle positioned on the exterior of the releasable wrapper 34 or the interior of the releasable wrapper 34. The receptacle containing the wipe 80 may cover the entire length of the releasable wrapper 34 or just part of the length of the releasable wrapper 34 depending on the size of the wipe 80, and manner of folding the wipe.

The receptacle 94 shown in FIG. 14 lays on the surface of the sanitary napkin before the sanitary napkin is folded over. The receptacle 94 shown in FIG. 15 is preferably releasably attached to the outside surface of the releasable wrapper 34 by any known means such as releasable adhesives, mechanical fasteners, and the like.

Figure 16:
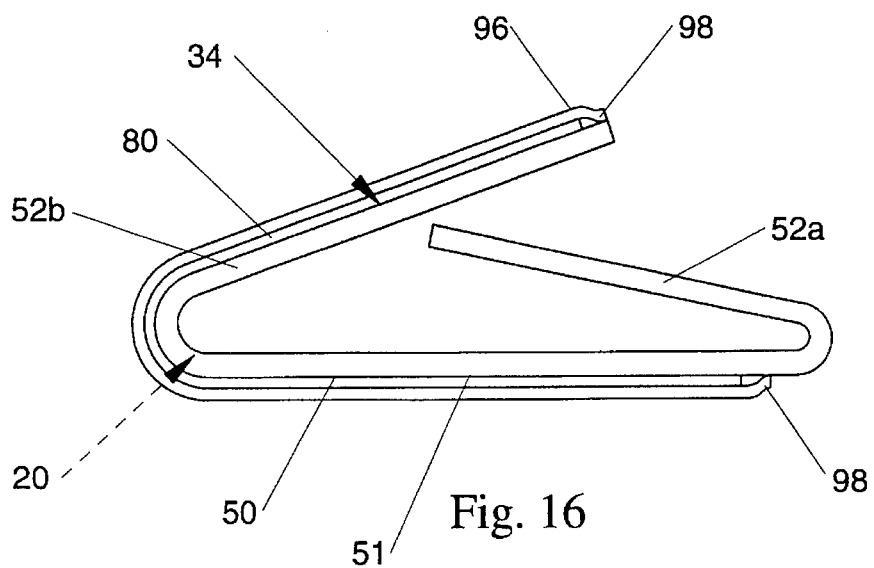
FIG. 16 is a sectional view similar to FIGS. 14 and 15 which shows an alternative sanitary napkin wrapper having a cleansing wipe adjacent a face of the wrapper.

FIG. 16 shows an embodiment in which the wipe 80 is laminated between the releasable wrapper 34 and a covering, such as a film 96.

The wipe 80 shown in FIG. 16 is preferably positioned between the releasable wrapper 34 and the covering before the wrapper 34 and sanitary napkin 20 are folded. In this embodiment, the longitudinal and end edges of the film 96 and the wrapper 34 extend beyond those of the wipe 80 to form a peripheral area 98. The wrapper 34 and film 96 are sealed about this peripheral area 98 with the wipe 80 in between. In this embodiment, (as in all the other embodiments described herein), the film 96 or other material in which the wipe 80 is sealed should be provided with barrier properties to keep liquids and vapors from evaporating from the wipe 80 prior to use. This embodiment has the advantage that the wipe 80 can be packaged with no or minimal folding of the wipe.

Figure 17:
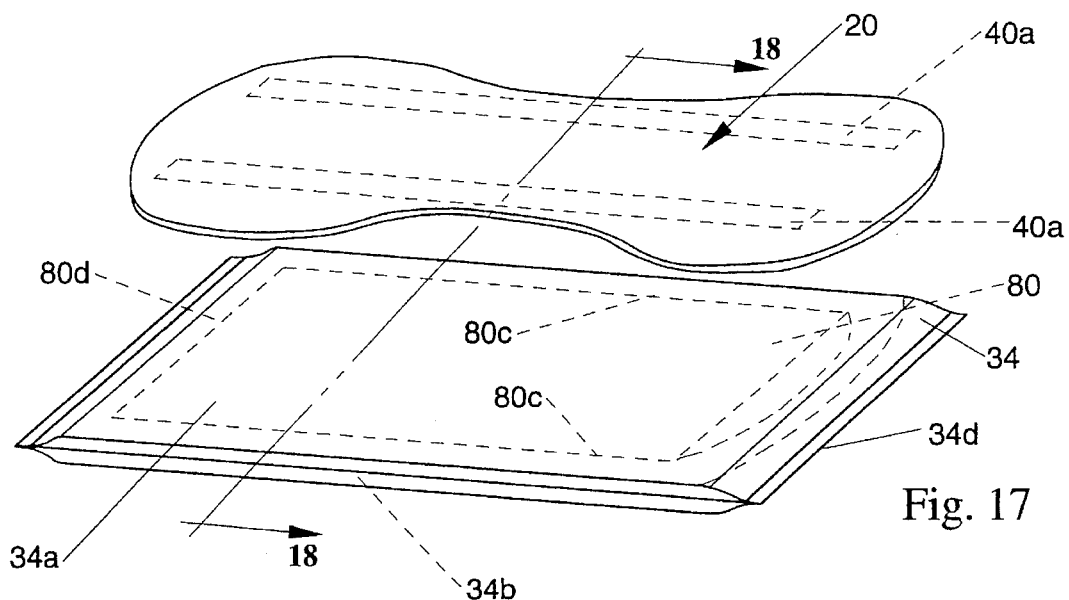
FIGS. 17 and 18 are a disassembled perspective view and a cross-section view of another sanitary napkin wrapper for packaging a cleansing wipe.
Figure 18:
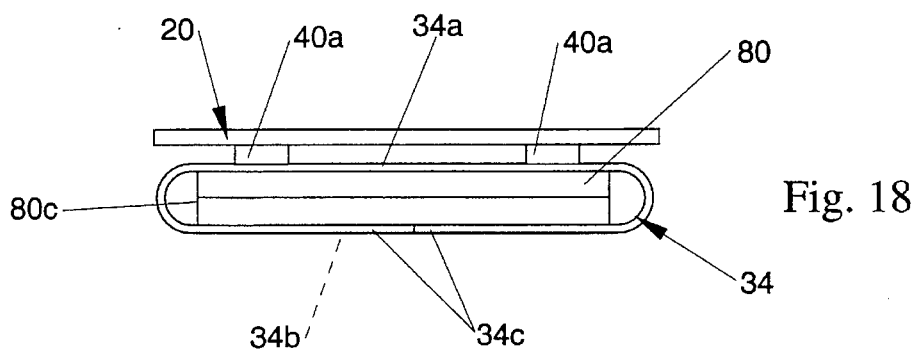

FIGS. 17 and 18 show a variation of the embodiment shown in FIG. 16. Instead of being laminated between the releasable wrapper 34 and a film, the wipe 80 is completely wrapped by the releasable wrapper 34. The releasable wrapper 34 forms a releasable wrapper package that both: (1) holds the wipe 80, and (2) has a large enough surface area to cover the panty adhesive 40a.

The releasable wrapper 34 shown in FIGS. 17 and 18 has dimensions larger than the folded or unfolded cleansing wipe 80, as the case may be. The releasable wrapper 34 is preferably comprised of a single sheet of liquid and vapor impervious material. The cleansing wipe 80 is placed adjacent one of the faces of the unfolded releasable wrapper 34. The wipe 80 is positioned near the center of the wrapper 34 so that the longitudinal and end edges of the releasable wrapper 34 extend beyond the edges of the cleansing wipe 80.

FIG. 18 shows that the longitudinal edges 34c of the releasable wrapper 34 are then folded around the longitudinal edges 80c of the cleansing wipe 80 in a C-fold configuration. The longitudinal edges 34c of the releasable wrapper 34 may meet as shown in FIG. 18, or overlap. The longitudinal edges 34c of the wrapper 34 are sealed, preferably with a releasable seal.

The ends 34d of the folded releasable wrapper 34 material extend beyond the end edges 80d of the cleansing wipe 80 and are also sealed. The ends 34d of the releasable wrapper 34 can be sealed permanently or releasably. Providing a releasable seal at the ends 34d provides an alternative way of removing the cleansing wipe 80 from the wrapper package.

The releasable wrapper 34 package shown in FIGS. 17 and 18 preferably has one side or face that is coated with a release coating. In FIGS. 17 and 18, this is the side of the package designated 34a that is facing upward toward the top of the drawing page. The side of the releasable wrapper 34 facing upward is attached to the adhesive strips 40a on the backsheet of the sanitary napkin.

In other less preferred alternatives, the other side of the releasable wrapper package, the side formed with the longitudinal edges 34c of the wrapper 34 thereon, could be coated with the release coating and attached to the adhesive strips 40a.

While it is not necessary to thereafter fold the sanitary napkin 20 and wrapper 34 in the embodiment shown in FIGS. 17 and 18, the sanitary napkin and wrapper could be bi-folded, tri-folded, or configured in any other manner described herein.

The releasable wrapper 34 package shown in FIGS. 17 and 18 has the advantage that not only does it not require folding of the cleansing wipe 80, it can also be removed from the sanitary napkin and carried as a discrete package after the sanitary napkin 20 is put on by the wearer.

Figure 19:
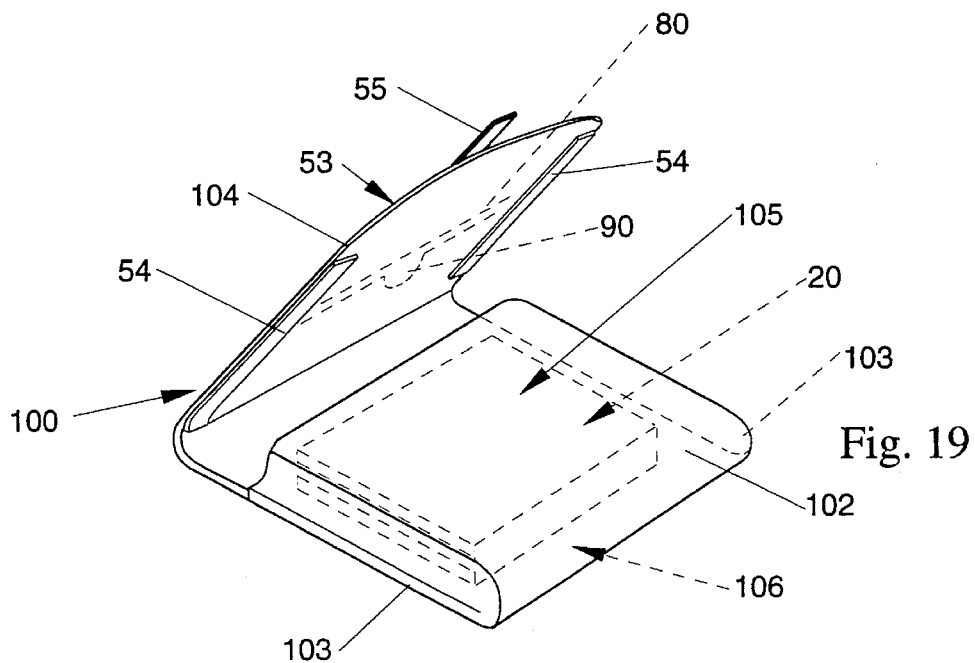
FIG. 19 is a perspective view of a package for a sanitary napkin that has a flap (or pouch) located thereon in which a cleansing wipe may be placed.

FIG. 19 shows another alternative embodiment for packaging a cleansing wipe with a sanitary napkin 20.

The package 100 shown in FIG. 19 is referred to as a "fold and wrap" package. The fold and wrap package 100 is a discrete package that has a package body 10 2 and a package flap 104. The sanitary napkin 20 is folded or rolled up and placed within the package body 102. The main difference between this embodiment, and the other embodiments described herein is that the fold and wrap package is not folded or rolled up with the sanitary napkin. Therefore, it does not replace the release paper conventionally used to cover the adhesive 40a on the garment-facing side 20b of the sanitary napkin 20. A conventional release paper is generally used with the sanitary napkin 20.

Another difference in the fold and wrap package lies in the sealing of the longitudinal side edges of the package. Typically, a permanent seal (i.e., a non-frangible seal) is used along the portion of the package that forms the package body 102. This seal is designated 103. The longitudinal edges of the package flap 104 may be frangibly sealed to the package body 102, such as by crimping, heat and/or pressure seals, or adhesive strips 54.

The cleansing wipe 80 is placed in a pouch 53 positioned on the fold and wrap package 100. The pouch 53 can be positioned on either the package body 102 or the package flap 104. The pouch 53 may be positioned in any suitable location on the package 100. The pouch 53, thus, may be positioned in locations that are similar to any of those specified above for the releasable wrapper 34. The pouch 53 should preferably have the same or similar properties to those properties described above for the pouches used on the other types of packages.

In alternative embodiments, the cleansing wipe 80 may be placed in a separate receptacle 94 similar to that described herein with reference to FIGS. 14 and 15. Such a separate receptacle can be permanently or removably attached to the fold and wrap package 100.

Preferably, the pouch 53 or receptacle 94 is located on the outside surface of the flap 104 of the fold and wrap package 100 (as shown in FIG. 19). Alternatively, the pouch 53 could be located on the front 105, or more preferably, the back 106, of the package body 102. These locations permit the pouch 53 containing the wipe 80 to be opened or the receptacle 94 containing the wipe 80 to be removed and used without opening the fold and wrap package. This is useful in the event the consumer needs to use the wipe 80, but not the sanitary napkin 20, and wishes to keep the sanitary napkin in a clean condition until ready for use.

It will be apparent to one skilled in the art that other variations are feasible and within the spirit and scope of the claimed invention. For example, combinations of the foregoing embodiments are feasible, and other means for maintaining the sanitary napkin 20 within the folded arrangement may be utilized. Additionally, other asymmetric arrangements may be utilized and adjustments in the relative sizes of the sanitary napkin 20 and releasable wrapper 34 may be made to accommodate the desired package size. All such variations are within the scope of the claimed invention.

In addition, while a preferred sanitary napkin embodiment of the present invention has been described, numerous other sanitary napkin embodiments could be provided with the fastening system and wrapper of the present invention. Some such sanitary napkins are disclosed in U.S. Pat. application Ser. No. 07/707,233 entitled "Sanitary Napkin Having Laterally Extensible Means for Attachment to the Undergarment of the Wearer", filed May 21, 1991 in the name of Osborn, et al., U.S. Pat. Nos. 5,009,653 and 4,950,264, issued to Osborn on Apr. 23, 1991 and Aug. 21, 1990, respectively, U.S. Pat. No. 4,917,697 entitled "Sanitary Napkin Having Flaps and Stress Relief Means" which issued to Osborn, III, et al. on Apr. 17, 1990, U.S. Pat. No. 4,687,478, entitled "Shaped Sanitary Napkin With Flaps", which issued to Van Tilburg on Aug. 18, 1987, U.S. Pat. No. 4,589,876, entitled "Sanitary Napkin", which issued to Van Tilburg on May 20, 1986, and U.S. Pat. No. 4,285,343, entitled "Sanitary Napkin", which issued to McNair on Aug. 25, 1981.

The wipe 80 in any of the embodiments described above may be similarly packaged with other types of pads, such as diapers, incontinent products, panty liners, as well as tampons, and other absorbent articles.

Suitable absorbent articles in the form of pantiliners are disclosed in U.S. Pat. No. 4,738,676 entitled "Pantiliner", issued to Osborn on Apr. 19, 1988. Suitable absorbent articles, at least some of which are in the form of adult incontinence products, are described in U.S. Pat. application Ser. Nos. 07/637,090 and 07/637,571 filed by John R. Noel, et al. and Barry R. Feist, et al. on Jan. 3, 1991.

Figure 20:
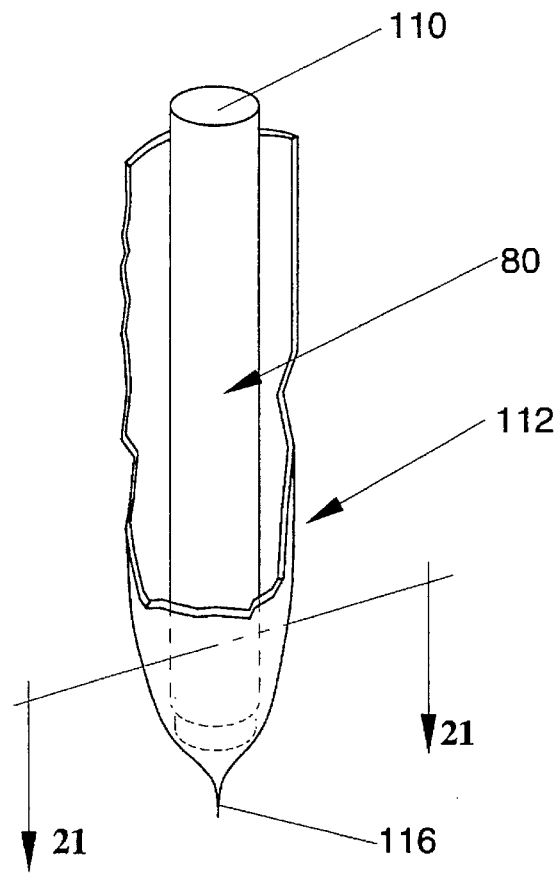
FIGS. 20 and 21 are perspective (with portions cut away) and end sectional views of a tampon package containing a cleansing wipe.
Figure 21:
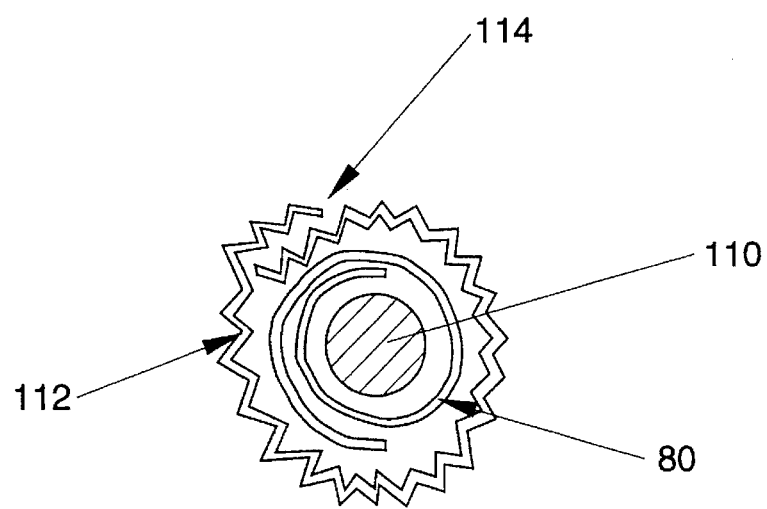

FIGS. 20 and 21 show an example of an embodiment for packaging a cleansing wipe 80 with a tampon 110. The tampon 110 can be in any known form. For purposes of illustration, an example of a tampon is disclosed in U.S. Pat. No. 4,475,911 issued to Gellert on Oct. 4, 1984.

The wipe 80 shown in FIGS. 20 and 21 is wrapped around the tampon 110. The wrapped tampon is wrapped with a moisture and vapor impervious overwrap 112. The side 114 and ends (one of which is shown as) 116 of the overwrap 112 are sealed. The tampon package is provided with a releasable seal at the side 114, and/or at least one of the ends 116 for use in opening the package.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An individually packaged sanitary napkin comprising:
   a sanitary napkin having a body-facing side, a garment-facing side, a length, a width, two longitudinal edges, and two end edges, said sanitary napkin comprising:
   a liquid pervious topsheet;
   a liquid impervious backsheet joined to said topsheet, said backsheet having opposed inwardly and outwardly oriented faces;
   an adhesive fastener on said outwardly oriented face of said backsheet;
   an absorbent core positioned between said topsheet and said backsheet;
   a releasable wrapper releasably affixed to the adhesive fastener on said outwardly oriented face of said backsheet, said releasable wrapper having a longitudinal dimension, a transverse dimension, an inwardly oriented face, an outwardly oriented face, a pair of longitudinal side edges, a pair of end edges, and a pair of ends, wherein only said releasable wrapper is folded about a longitudinal axis adjacent at least one of said longitudinal edges of said sanitary napkin in a C-fold thereby wrapping said at least one of said longitudinal edges, and wherein said sanitary napkin and said releasable wrapper are folded about two transverse axes which form said wrapper into first, second, and third trisections, wherein said first trisection is folded over said second trisection to form a package body and said third trisection is folded over said first trisection to form a package flap;
   a pouch disposed on one of said faces of said wrapper and positioned entirely within one of said trisections said pouch comprising a first portion of said wrapper and a thin flexible material having sides that are joined to said first portion of said wrapper with a seal, at least a portion of said seal being releasable; and
   a cleansing wipe positioned inside said pouch.

2. The individually packaged sanitary napkin of claim 1 wherein said cleansing wipe is a liquid-containing wipe.

3. The individually packaged sanitary napkin of claim 2 wherein said at least a portion of said seal which is releasable comprises a pressure-sensitive adhesive seal.

4. The individually packaged sanitary napkin of claim 3 wherein said at least a portion of said seal which is releasable defines an openable edge of said pouch, said pressure-sensitive adhesive seal has a centerline, and said pressure-sensitive adhesive seal is configured so that portions of said pressure-sensitive adhesive adjacent the centerline of said seal are closer to the openable edge of said pouch than are the remaining portions of said pressure-sensitive adhesive.

5. The individually packaged sanitary napkin of claim 4 wherein said pressure-sensitive adhesive seal has a convex configuration.

6. The individually packaged sanitary napkin of claim 5 wherein the openable edge of said pouch has a convex configuration.

7. The individually packaged sanitary napkin of claim 6 wherein said pouch is provided with a tab along the openable edge of said pouch for use in opening said pouch and removing said cleansing wipe.

8. The individually packaged sanitary napkin of claim 1 wherein said cleansing wipe is removable from said pouch and said pouch is usable for disposing of at least one of said sanitary napkin or cleansing wipe after use.

9. The individually packaged sanitary napkin of claim 1 wherein said pouch is located in said first trisection on the outwardly oriented face of said wrapper.

10. The individually packaged sanitary napkin of claim 1 wherein said pouch is located in said second trisection on the outwardly oriented face of said wrapper.

11. The individually packaged sanitary napkin of claim 1 wherein said pouch is located in said third trisection on the outwardly oriented face of said wrapper.

12. The individually packaged sanitary napkin of claim 1 further comprising a tape fastening system a portion of which is disposed on said package body and a portion of which is disposed on said package flap, for releasably securing said package flap to said body in a folded arrangement.

13. The individually packaged sanitary napkin of claim 1 wherein said pouch is located in said third trisection on the inwardly oriented face of said wrapper.

14. The individually packaged sanitary napkin of claim 1 wherein said thin flexible material comprises a second portion of said releasable wrapper extending from said first portion of said wrapper which is folded over said first portion of said releasable wrapper.

* * * * *

UNITED STATES PATENT AND TRADEMARK OFFICE
CERTIFICATE OF CORRECTION

PATENT NO. : 5,569,230
DATED : October 29, 1996
INVENTOR(S) : DANIELLA J. FISHER et al.

It is certified that error appears in the above-identified patent and that said Letters Patent is hereby corrected as shown below:

Column 6, lines 61-62, "en sure" should read -- ensure --.

Column 7, line 34, "enough" should read -- inward --.

Column 14, line 39, "relation ship" should read -- relationship --.

Column 17, line 59, "herein" should read -- herein) --.

Column 17, line 65, "Instill" should read -- In still --.

Column 18, line 22, "53eis" should read -- 53e is --.

Column 22, line 9, "relation ship" should read -- relationship --.

Column 22, line 59, "Instill" should read -- In still --.

Column 24, line 27, "10 2" should read -- 102 --.

Column 26, line 36, "trisections" should read -- trisections, --.

Column 27, line 13, "system" should read -- system, --.

Signed and Sealed this

Twenty-first Day of December, 1999

Attest:

Q. TODD DICKINSON

*Attesting Officer*  *Acting Commissioner of Patents and Trademarks*